US012778895B2

(12) United States Patent
Gupta et al.

(10) Patent No.: US 12,778,895 B2
(45) Date of Patent: Nov. 3, 2026

(54) COMPOSITIONS FOR MODIFIED RELEASE OF ACTIVE INGREDIENTS

(71) Applicant: PROLEVI BIO AB, Lund (SE)

(72) Inventors: Sahil Gupta, Idstein (DE); Daniel Bar-Shalom, Odense C (DK)

(73) Assignee: PROLEVI BIO AB, Lund (SE)

( * ) Notice: Subject to any disclaimer, the term of this patent is extended or adjusted under 35 U.S.C. 154(b) by 173 days.

(21) Appl. No.: 18/858,476

(22) PCT Filed: Apr. 20, 2023

(86) PCT No.: PCT/EP2023/060373
§ 371 (c)(1),
(2) Date: Oct. 21, 2024

(87) PCT Pub. No.: WO2023/203173
PCT Pub. Date: Oct. 26, 2023

(65) Prior Publication Data

US 2025/0262160 A1 Aug. 21, 2025

(30) Foreign Application Priority Data

Apr. 22, 2022 (EP) .................................... 22169513
Nov. 24, 2022 (EP) .................................... 22209460

(51) Int. Cl.
*A61K 9/20* (2006.01)
*A61K 31/4045* (2006.01)
*A61K 38/22* (2006.01)

(52) U.S. Cl.
CPC .......... *A61K 9/2031* (2013.01); *A61K 9/2054* (2013.01); *A61K 31/4045* (2013.01); *A61K 38/22* (2013.01)

(58) Field of Classification Search
CPC ........ A61K 9/2031; A61K 9/2054; A61P 5/14
See application file for complete search history.

(56) References Cited

U.S. PATENT DOCUMENTS

2006/0246133 A1 11/2006 Beasley et al.
2008/0138404 A1* 6/2008 Walsh et al.
2010/0136109 A1* 6/2010 Ross et al.

FOREIGN PATENT DOCUMENTS

WO WO1999/43307 A1 9/1999
WO WO2000/42959 A1 7/2000
WO WO2008/129303 A2 10/2008
WO WO2010/018408 A1 2/2010
WO WO 2010018408 A2 * 2/2010
WO WO2013/096596 A1 6/2013
WO WO2021/146016 A1 7/2021

OTHER PUBLICATIONS

Pharmaceuticals for oral cavities, Jan. 26, 1985; retrieved from STN; XP002809618 (Year: 1985).
Bowerbank S., et al., Dissolution Testing of Single- and Dual-Component Thyroid Hormone Supplements, Separations, 6(1):18, 2019.
Carlé A., et al., Hypothyroid Patients Encoding Combined MCT10 and DIO2 Gene Polymorphisms May Prefer L-T3 + L-T4 Combination Treatment—Data Using a Blind, Randomized, Clinical Study, Eur Thyroid J., 6(3):143-151, Jul. 2017.
Dumitrescu, A., et al., Extended Absorption of Liothyronine from Poly-Zinc-Liothyronine: Results from a Phase 1, Double-Blind, Randomized and Controlled Study in Humans, Thyroid, 32(2); 196-205, Feb. 2022.
Gamble, K. et al., Circadian clock control of endocrine factors, Nat Rev Endocrinol., 10(8):466-475, Aug. 2014.
Gergely, V., et al., Anti-haemorrhoidal suppositories—comprise polyoxythylene base, oxy:tetracycline, doxycycline, hydrocortisone and lidocaine or panthenol, Aug. 30, 1993, XP002424514.
Handbook of granulation technology, 2nd ed. International Standard Book No. 10: 0-8247-2647-2. Taylor and Francis, 2005.
Harpsøe, et al., Clinical pharmacokinetics of melatonin: a systematic review, European Journal of Clinical Pharmacology, 71: 901-909, 2015.
Hegedüs, L., et al., Primary hypothyroidism and quality of life, Nat Rev Endocrinol., 18(4): 230-242, Apr. 2022.
Jonklaas, J., et al., Single dose T3 administration: kinetics and effects on biochemical and physiological parameters, Ther Drug Monit., 37(1): 110-118, 2015.
Muñoz-Ortiz, J., et al., Prevalence of hyperthyroidism, hypothyroidism, and euthyroidism in thyroid eye disease: a systematic review of the literature, Syst Rev, 9:201, 2020, 12 pages.
Qureshi, S., In Vitro-In Vivo Correlation (IVIVC) and Determining Drug Concentrations in Blood from Dissolution Testing—A Simple and Practical Approach, The Open Drug Delivery Journal, 4: 38-47, 2010.
Russell, et al., Free triiodothyronine has a distinct circadian rhythm that is delayed but parallels thyrotropin levels, J. Clin. Endocrinol Meta., 93(6): 2300-2306, Jun. 1, 2008.
Taylor, P., et al., Global epidemiology of hyperthyroidism and hypothyroidism, Nat Rev Endocrinol., 14(5): 301-316, May 2018.
Van Tassell, et al., Pharmacokinetics of L-Triiodothyronine in Patients Undergoing Thyroid Hormone Therapy Withdrawal, Thyroid, 29(10): 1371-1379, Oct. 2019.
Virili, C., Gastrointestinal Malabsorption of Thyroxine, Endocrine Reviews, 40(1): 118-136, Feb. 2019.
Virili, C., et al., Levothyroxine Therapy in Gastric Malabsorptive Disorders, Front. Endocrinol, 11:621616, Jan. 2021.
Hu et al., The Properties of HPMC: PEO Extended Release Hydrophilic Matrices and their Response to Ionic Environments, Pharm. Res., 34(5): 941-956, 2017.

* cited by examiner

*Primary Examiner* — Robert A Wax
(74) *Attorney, Agent, or Firm* — Weston R. Gould; DINSMORE & SHOHL LLP

(57) ABSTRACT

The present disclosure relates to the field of sustained release compositions of active ingredients able to modulate endocrine or hormonal signalling and uses thereof. The formulations according to the present disclosure accommodate for chronotherapeutic events of fluctuating levels natural in signalling over a 24 hour period.

21 Claims, 12 Drawing Sheets

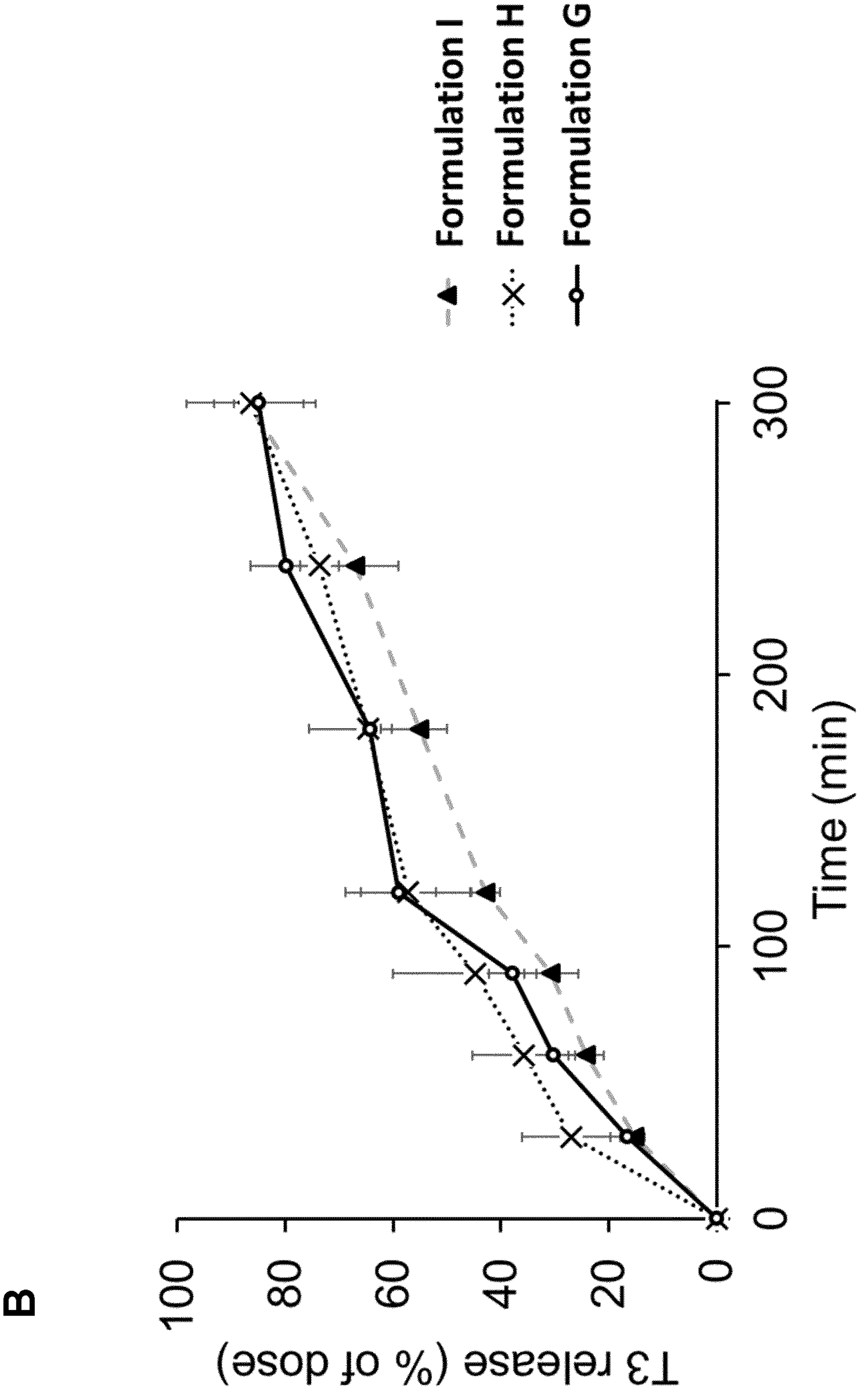
Fig. 4, cont.

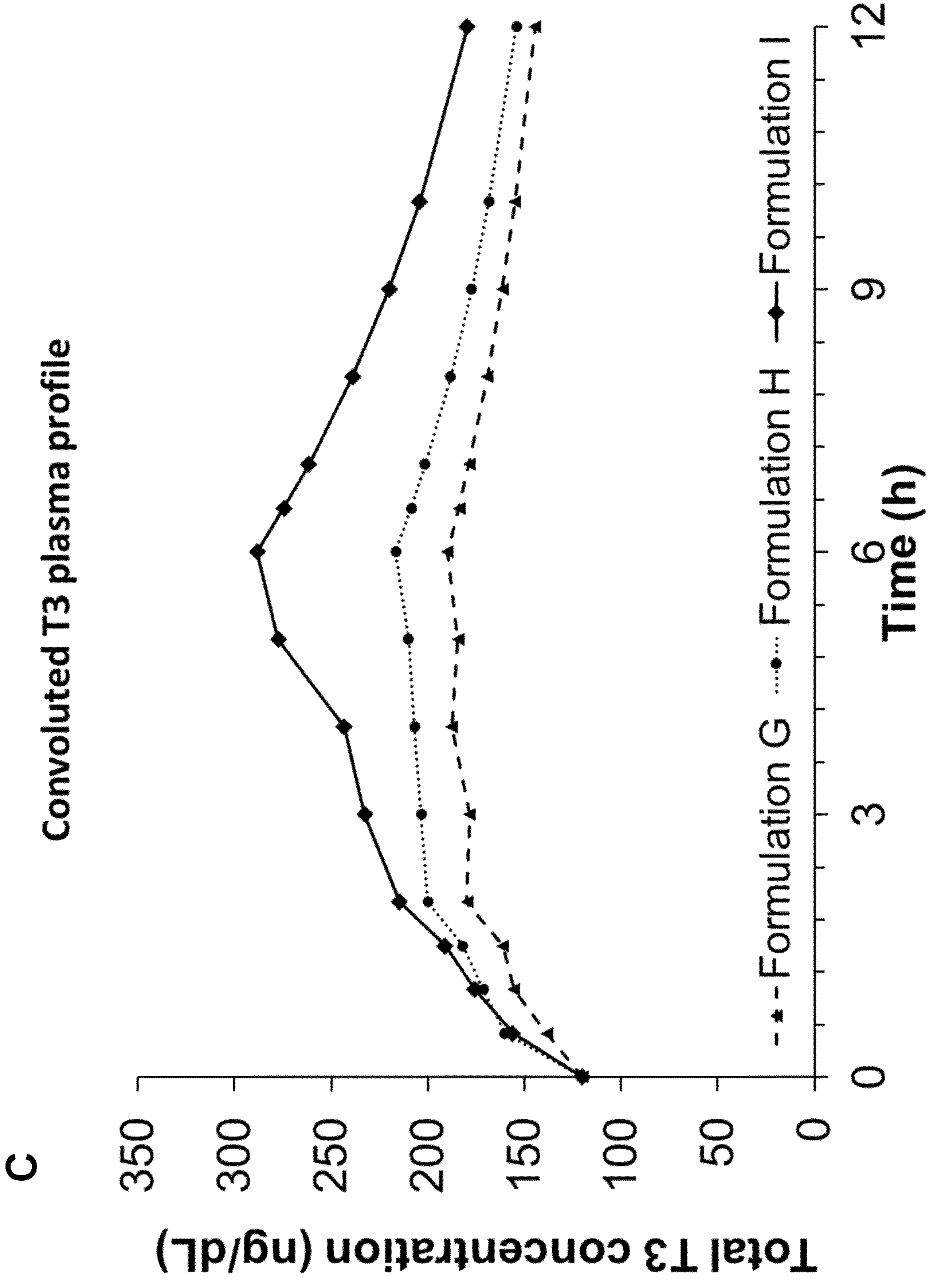
Fig. 4, cont.

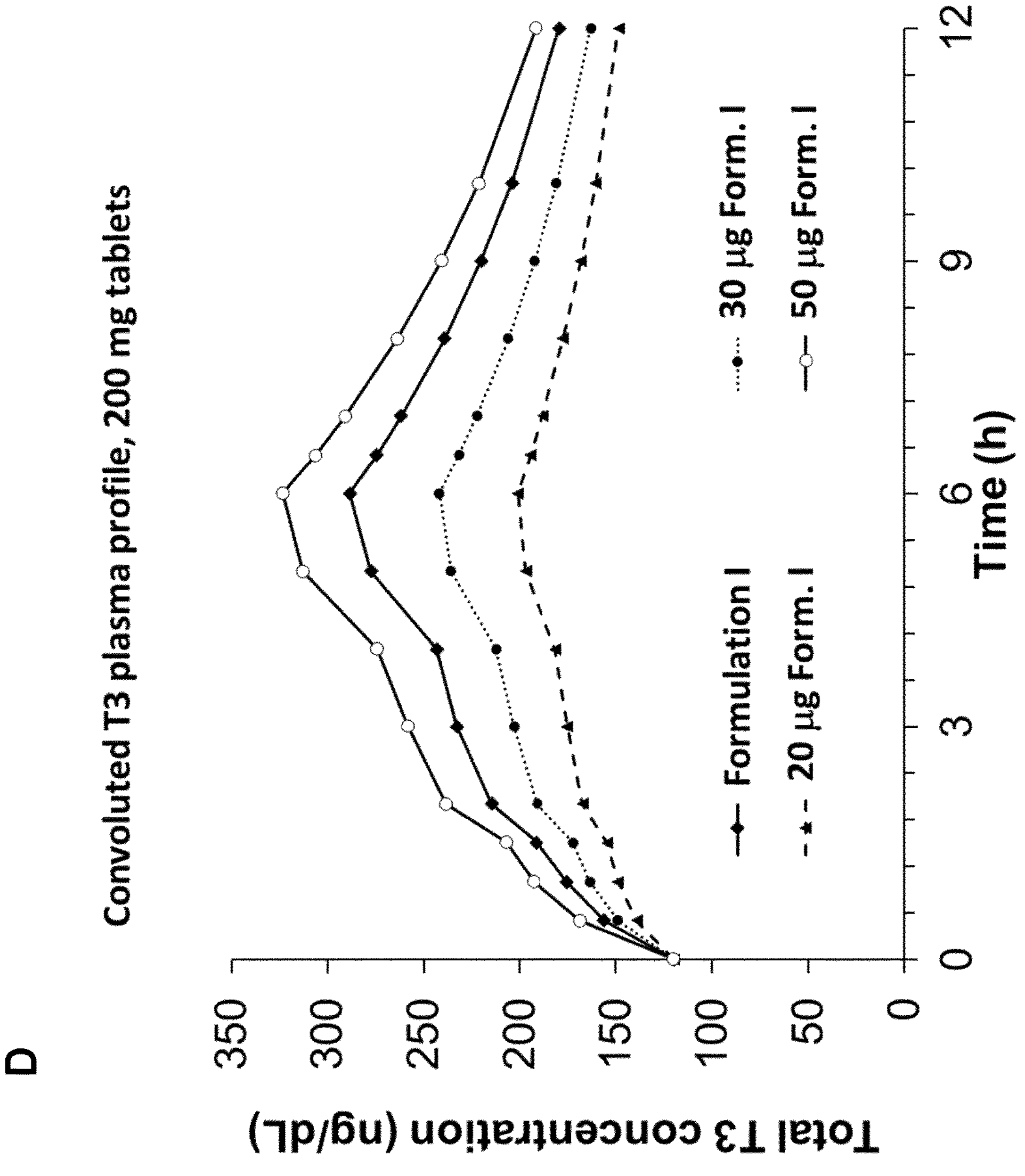
Fig. 4, cont.

E
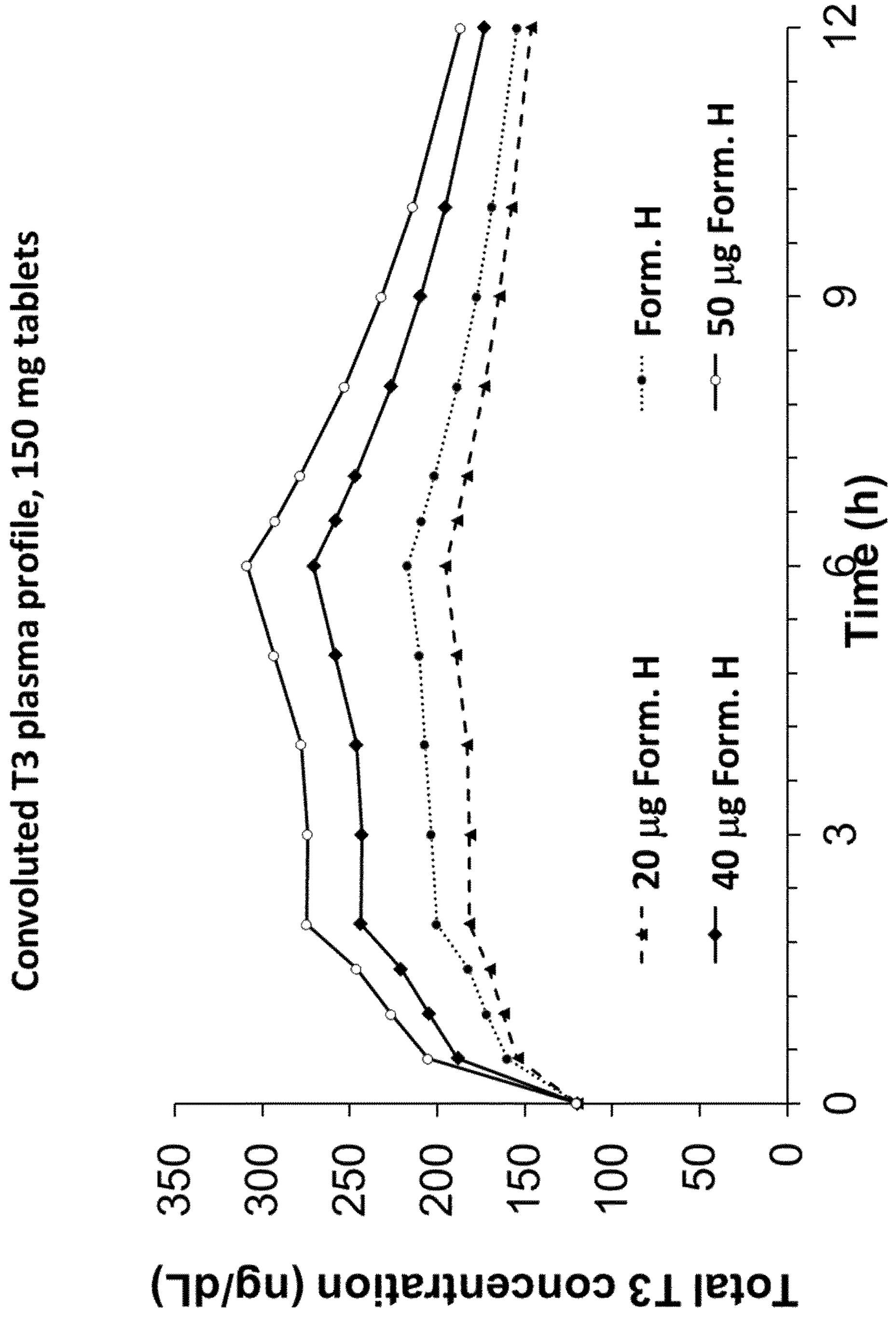
Fig. 4, cont.

F
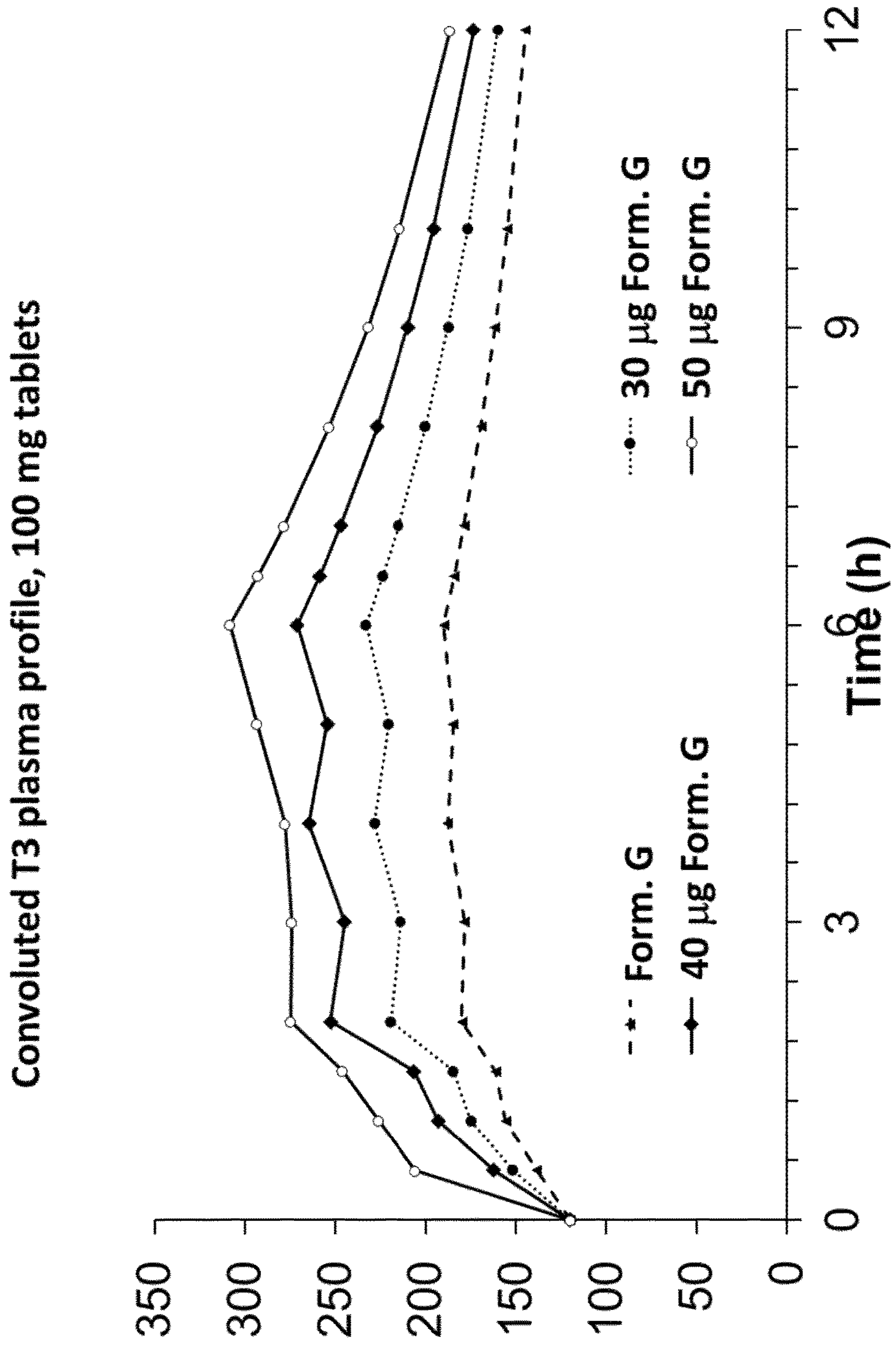
Fig. 4, cont.

COMPOSITIONS FOR MODIFIED RELEASE OF ACTIVE INGREDIENTS

CROSS REFERENCE TO RELATED APPLICATIONS

This application is a U.S. national stage under 35 U.S.C. § 371 of international application number PCT/EP2023/060373 filed Apr. 20, 2025, and which depends from and claims priority to European Patent Application No: 22169513.3 filed on Apr. 22, 2022 and European Patent Application No: 22209460.9 filed on Nov. 24, 2024, the entire contents of which are incorporated herein by reference.

TECHNICAL FIELD

The present disclosure relates to the field of sustained release compositions of active ingredients able to emulate or modulate endocrine or hormonal signalling and uses thereof. The formulations according to the present disclosure accommodate for chronotherapeutic events of fluctuating levels in natural signalling over a 24 hour period.

BACKGROUND

A great number of hormonal or endocrine signalling systems experience fluctuations over the course of the day. This has evolved through the imperative need of organisms to maintain biological processes within physiologic boundaries in adaptation to fluctuation of daily stimuli. Not only circulating level of endocrine factors oscillates over the 24 hour period, but so does responsiveness of target receptors and tissues to said factors.

Hormonal factors and systems such as cortisol, growth hormone, testosterone, prolactin, thyroid stimulating hormone, triiodothyronine, renin-angiotensin-aldosterone system, fibroblast growth factor 21, ghrelin, adiponectin, leptin, vasopressin, insulin or melatonin are known to oscillate with a periodicity of 24 hours in humans. The oscillation for these systems is time-of-day dependant[12].

This poses a unique challenge from a therapeutic perspective for active ingredients able to modulate these systems. Achieving therapeutically effective doses in subjects that accommodate this oscillation is not trivial. This is especially true for systems for which the signaling increases or decreases in the middle of the night or early in the morning, since dosing of active ingredients at times before is not possible or highly inconvenient for the patients.

Providing pharmaceutical formulations able to release active ingredients in a way that accommodates these fluctuating levels is highly desirable and could benefit patients suffering from multiple conditions. This is especially true for patients under chronic or long-term treatment. Therefore, there is currently a need in the field to develop such formulations.

For example, thyroid disorders—Hypothyroidism (HOT) and Hyperthyroidism (HT)—affect over 10% of the global population, are highly prevalent in age groups above 65 years, and 10 times more prominent in women[1]. Thyroid hormone levels oscillate in the body according to a circadian rhythm, with a natural oscillation following the day and night cycles. In a healthy individual, concentrations of triiodothyronine (T3) naturally increase progressively during the night, and return to baseline in the morning[4].

Current treatments involve the use of triiodothyroxine (T4) and T3. T4 is an inactive hormone and is converted into T3 in the body by two enzyme deiodinase. T3 is the active hormone that controls cell metabolism, heart rate, body temperature, peristalsis, muscle contractions and apoptosis. 80% of patients on current hypothyroidism therapy reportare dissatisfied with the current treatments, 60% of these report poor quality of life (QoL), tiredness, weight gain and are generally over treated resulting in long-term side effects[2]. 10-20% patients of these do not respond to LT4 monotherapy due to known/unknown underlying genetic factors (e.g. mutations in enzymes converting T4 to T3 e.g. DiO2 T92A, or thyroid hormone transporters e.g. MCT10), but a vast majority[3] prefer the co-administration of T3[4].

Today T3 is administered as immediate release (LT3), which does not mimic the natural circadian oscillation rhythm. Treatment with T3 has historically failed due to short half-life (elimination half-life of T3 is 23-25 h in adults, the biological half-life is 2.5 days and an estimated baseline corrected half-life is 4 hours[11] and adverse effects. As seen in studies with thyroidectomized patients (i.e. with no endogenous T4 or T3)[15] and administered exogenous LT4 or LT3, which have a $T_{1/2}$ half-life of 3.62 hrs, Tmax 2.9 hrs i.e. 11 days after last LT3 dose withdrawal[15]. The short half-life leads to dosing multiple times a day and thereby poor patient compliance. This often leads to long-term overdosing and severe side effects such as cardiovascular diseases, hypertension, mineral metabolism complications and more.

Currently, there are no commercially available delayed-release T3 drug in the market as a standard replacement for T4 monotherapy. Attempts to design extended-release formulations of T3 able to mimic circadian rhythm profiles have not been satisfactory, since extended-release attempts in the past do not return to natural baseline levels and increase the probability of overdosing and inducing side effects.

Thus, there is currently a need in the art for sustained release T3 formulation able to respect the natural oscillation in hormone levels and provide alternatives to currently inefficient hypothyroidism treatments, ideally avoiding the physiological pitfalls[8].

SUMMARY

The present disclosure addresses the above-mentioned issues by providing improved sustained-release compositions and formulations of active ingredients able to emulate or modulate hormonal or endocrine signalling respecting the natural oscillation in hormone levels according to the circadian rhythm.

Thus, in one aspect, the present disclosure relates to compositions and pharmaceutical formulations comprising:

a. an active ingredient or a pharmaceutically acceptable salt thereof,
b. hydroxypropyl methyl cellulose acetate succinate (HPMC-AS) and/or hydroxypropyl methyl cellulose (HPMC) in a total amount of 0.1% to 20% by weight, and
c. polyethylene oxide (PEO) in an amount from 80 to 99.9% by weight.

The inventors have surprisingly found that formulations according to the disclosure herein display a dissolution profile and release of the active ingredient that matches the physiological levels of natural hormone signalling according to the day and night cycles with a safe return to base line levels.

One aspect of the present disclosure provides for a method of manufacturing a composition comprising the steps of:

a. preparing a melt uniform dispersion comprising i) PEO, ii) hydroxypropyl methyl cellulose and/or HPMC-AS and iii) an active ingredient or a pharmaceutically acceptable salt thereof, and
b. cooling the melt to obtain a solid composition.

In one aspect, the present disclosure provides for a method of manufacturing a composition comprising the steps of:

i. mixing powders of an active ingredient or a pharmaceutically acceptable salt thereof, HPMC and/or HPMC-AS and PEO, and
ii. compacting the mixture to obtain uniform dispersion of components in a matrix.

In another aspect, the present provides for a composition or pharmaceutical formulation as described herein for use as a medicament.

In another aspect, the present disclosure provides for a composition or pharmaceutical formulation as described herein for use in the modulation able to modulate hormonal or endocrine signaling.

In another aspect, the present disclosure relates to the use of a composition or pharmaceutical formulation as described herein for treatment of hypothyroidism and/or for use to prevent or reduce the incidence of side effects associated with hypothyroidism treatments.

DEFINITIONS

Figure 1:
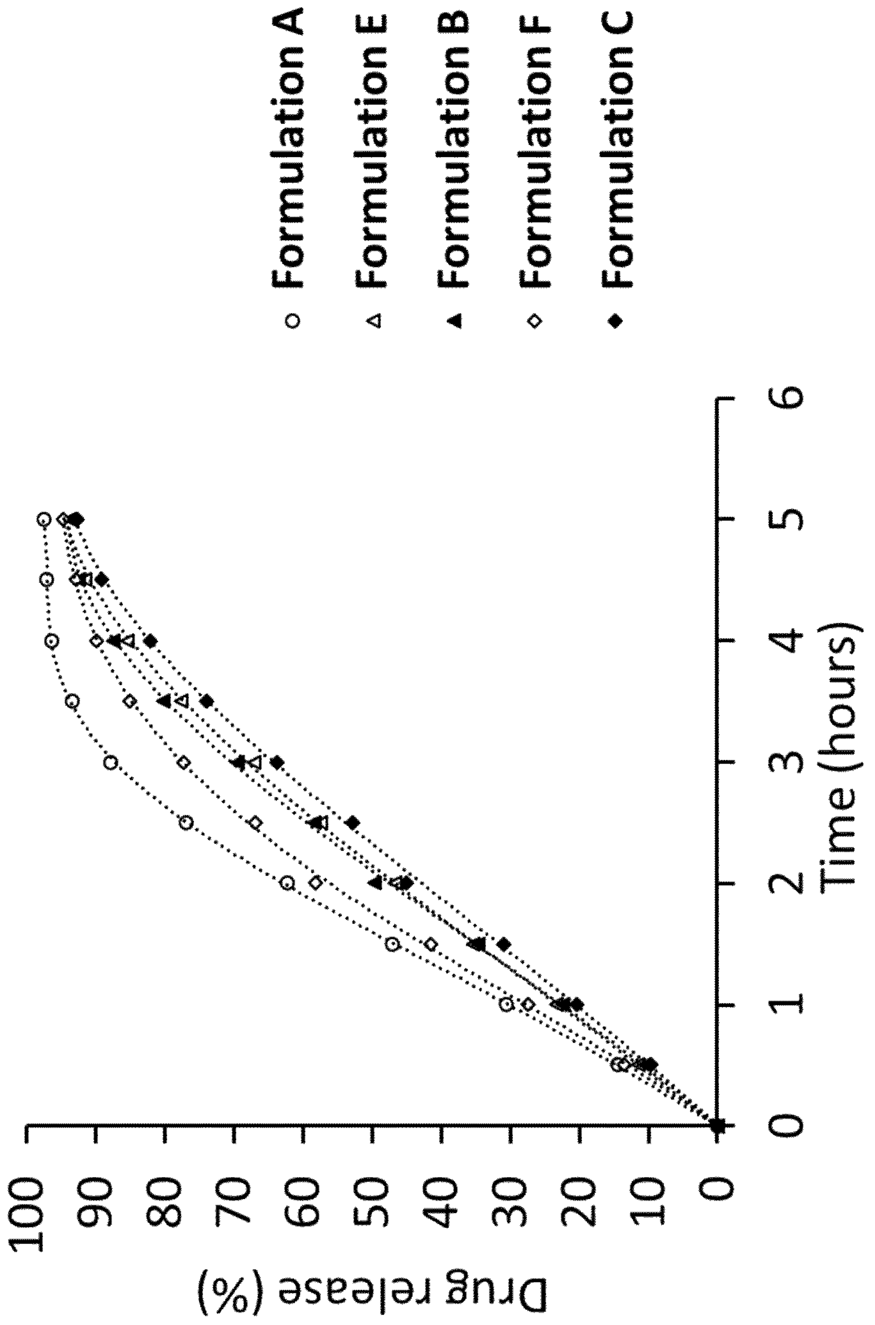
FIG. 1. Dissolution profiles of ibuprofen as T3 model compound displayed by formulations A, B, C, E and F.

"Cmax" is a term used in pharmacokinetics to refer to the maximum (or peak) serum concentration that a drug achieves in a specified compartment or test area of the body after the drug has been administrated and prior to the administration of a second dose.

"Tmax" is the term used in pharmacokinetics to describe the time at which the Cmax is observed.

"Half-life ($t_{1/2}$)" is a term that refers to the time required for half of the drug in blood to be eliminated.

"Apparent volume of distribution (Vd)" or "Apparent volume of drug distribution" is a parameter calculated from amount of drug administered and its observed concentration (mass/volume) for an individual with given body mass.

"Oral bioavailability" refers to the fraction of orally administered drug available in the blood calculated relative to drug concentration after intravenous injection.

"Sustained release" is a term used to refer to a mechanism used in compositions or formulations to provide release of a drug or an active pharmaceutical ingredient from the composition or formulation over an extended period time, as opposed to all at once, or as opposed to an immediate release or a burst release. In some embodiments, as used herein, the terms "sustained release", "extended release", "controlled release" and "modified release" are interchangeable to refer to this mechanism.

In some embodiments, as used herein, the terms "composition" and "formulation" are used interchangeably.

An "active ingredient" as used herein refers to any component that provides pharmacological activity or other direct effect in the diagnosis, cure, mitigation, treatment, or prevention of disease, or to affect the structure or any function of the body of man or animals.

By "hormones" or "endocrine factors" it is referred to substances produced by organs of the body that travel by blood to trigger activity in other locations, or synthetic compounds that have the same activity as a natural hormone.

By "hormonal signalling" or "endocrine signalling" it is referred to hormone receptor inhibition of activation. Hormonal signalling is modulated by natural hormones, or other compounds that have the same activity as a natural hormone.

The term "about" as used herein to refer to an amount or percentage is to be interpreted as a variation of ±10% with respect the value of the amount or percentage it refers to, such as ±5%.

"Matrix" as used herein refers to a well-mixed composite of one or more active ingredients with one or more excipients, especially polymers.

DETAILED DESCRIPTION OF THE INVENTION

The present invention relates to sustained-release pharmaceutical compositions and formulations of active ingredients able to modulate hormonal or endocrine signalling respecting the natural oscillation during a 24-hour period according to the circadian rhythm.

Thus, one aspect of the present disclosure relates to pharmaceutical compositions and pharmaceutical formulations comprising:

a. an active ingredient or a pharmaceutically acceptable salt thereof, b. hydroxypropyl methyl cellulose acetate succinate (HPMC-AS) and/or hydroxypropyl methyl cellulose (HPMC), and c. polyethylene oxide (PEO).

Another aspect of the present disclosure relates to compositions and formulations as described herein for use as a medicament.

In one aspect the present disclosure relates to compositions and formulations as described herein for use in the treatment of hypothyroidism and/or for use to prevent or reduce side effects associated with hypothyroidism treatments.

The inventors have surprisingly shown that the compositions disclosed herein provide for a dissolution rate and release profile of the active ingredient that is adequate to modulate hormonal and endocrine signalling levels according to the natural oscillation in hormonal or endocrine signalling of different systems during a 24 hour period with a safe return to baseline.

This is advantageous for hormonal or endocrine signalling which signalling increases or decreases during the night or throughout early morning, as dosage of active ingredients at those times is inconvenient for patients. Additionally, the sustained release provides for concentrations that better match the natural levels throughout these time periods. Thus, the compositions according to the present disclosure have great potential to provide the active ingredient according to the patients' needs, leading to better therapeutic outcomes, reduction of side-effects and/or improved quality of life—especially for patients requiring chronic treatments.

The advantages of the formulations and compositions disclosed herein are numerous and include:

- Reduced number of doses required and simplified administration regimes compared to standards of treatment, leading to better patient compliance.
- Possibility to combine formulations according to the present invention with standard of care treatments.
- Improved quality of life in patients experiencing difficulties with current standards of care treatments.

Pharmaceutical Composition

Sustained or controlled release technology is a collection of mechanisms, such as erosion and diffusion, used in compositions or formulations to slowly dissolve and release or slowly release and dissolve a drug over time. Extended-release formulations may be taken less frequently than immediate-release formulations, and they usually keep steadier levels of the drug in the bloodstream.

Sustained release compositions may be prepared such that the active ingredient is embedded in a matrix of substance(s) such that the dissolving drug must find its way out through the holes in the matrix. In some formulations, the drug dissolves into the matrix, and the matrix physically swells to form a gel, allowing the drug to exit through the gel's outer surface. In other cases, the matrix of substances slowly disaggregates and erodes, releasing the drug with a sustained release profile.

The inventors have shown that compositions comprising a an active ingredient and a matrix comprising: hydroxypropyl methyl cellulose (HPMC) and/or hydroxypropyl methyl cellulose acetate succinate (HPMC-AS) and polyethylene oxide (PEO); provide sustained release of the active ingredient with a desirable profile for active ingredients able to modulate endocrine or hormonal physiological levels that oscillate periodically over 24 hours according to day and night cycles with a safe return to base line.

Thus, in one embodiment the present disclosure relates to a pharmaceutical composition comprising:

a. an active ingredient or a pharmaceutically acceptable salt thereof, b. hydroxypropyl methyl cellulose acetate succinate (HPMC-AS) and/or hydroxypropyl methyl cellulose (HPMC), and c. polyethylene oxide (PEO).

The inventors have shown that pharmaceutical compositions comprising PEO, HPMC and/or HPMC-AS in specific amounts provide sustained release of the active ingredient a desirable profile according to physiological levels of endocrine or hormonal signalling that oscillates within a 24 hour period according to day and night cycles.

Polyethylene oxide (PEO) is obtained by polymerization of ethylene oxide. It has a similar structure than polyethylene glycol (PEG) which is obtained by condensation of ethylene glycol molecules. In this text, terms "PEG" and "PEO" are used interchangeably.

HPMC and HPMC-AS are cellulose derivatives wherein some free hydroxyl groups in cellulose have been substituted with hydroxypropyl and methyl groups. In the case of HPMC-AS, further hydroxyl groups are substituted with acetate and succinate groups. Generally, these materials are used as coatings to delay the release of a medicinal compound into the digestive tract.

In one embodiment, the HPMC-AS comprises 4 to 28% by weight succinyl groups and 2 to 16% by weight acetyl groups, for example 8 to 20% by weight succinyl groups and 4 to 12% by weight acetyl groups, for example 14 to 18% by weight succinyl groups and 4 to 9% by weight acetyl groups. In one embodiment, the acetyl content in the HPMC-AS is below 12% by weight, such as below 10% and the succinyl content is above 6% by weight, such as above 8% by weight.

Thus, in one embodiment the present disclosure relates to a pharmaceutical composition comprising:

a. an active ingredient or a pharmaceutically acceptable salt thereof, b. hydroxypropyl methyl cellulose acetate succinate (HPMC-AS) and/or hydroxypropyl methyl cellulose (HPMC) in a total amount of 0.1% to 20% by weight, and c. polyethylene oxide (PEO) in an amount from 80 to 99.9% by weight.

In another embodiment, the composition comprises HPMC and/or HPMC-AS in a total amount of about 1% to 20%, such as about 2% to 20%, such as about 5% to 15%, such as about 6% to 14%, such as about 7% to 13%, such as about 8% to 12%, such as about 9% to 11%, for example about 10%.

Additionally, the inventors have surprisingly shown that compositions comprising HPMC-AS mixed in a matrix, instead of as a coating or encapsulation, provides a sustained release profile with pharmacokinetic properties favorable for therapy with active ingredients that modulate hormonal or endocrine signaling of systems that oscillate within a 24 hour period. Furthermore, due to functional groups present in HPMC-AS, this component further provides improved protection to the active ingredient through diverse and varying conditions in the gastrointestinal track, especially pH.

In one embodiment, the composition does not comprise HPMC. For example, the composition is substantially free of HPMC.

Thus, in one embodiment, the composition comprises HPMC-AS in an amount of about 1% to 20% by weight, such as about 2% to 20%, such as about 5% to 15%, such as about 6% to 14%, such as about 7% to 13%, such as about 8% to 12%, such as about 9% to 11%, for example about 10%.

In one embodiment, the composition comprises HPMC-AS in an amount of about of 3% to 14% by weight, such as 3% to 4%, such as 4% to 5%, such as 5% to 6%, for example 6% to 7%, such as 7% to 8%, such as 8% to 9%, such as 9% to 10%, such as 10% to 11%, such as 11% to 12%, such as 12% to 13%, such as 13% to 14%. In one embodiment, the composition comprises HPMC-AS in an amount of about 5% to about 14% by weight. In one embodiment, the composition comprises HPMC-AS in an amount of about 8% to about 14% by weight.

In one embodiment, the composition does not comprise HPMC-AS.

In one embodiment, the composition comprises HPMC in an amount of about of about 1% to 20% by weight, such as about 2% to 20%, such as about 5% to 15%, such as about 6% to 14%, such as about 7% to 13%, such as about 8% to 12%, such as about 9% to 11%, for example about 10%.

In one embodiment, the composition comprises HPMC in an amount of about of 5% to 15% by weight, such as 5% to 6%, for example 6% to 7%, such as 7% to 8%, such as 8% to 9%, such as 9% to 10%, such as 10% to 11%, such as 11% to 12%, such as 12% to 13%, such as 13% to 14%, such as 14% to 15%, such as 15% to 16%, such as 16% to 17%, such as 17% to 18%, such as 18% to 19%, such as 19% to 20%.

In one embodiment, the PEO has an average molecular weight between 10 kDa to 2000 kDa, such as 50 kDa to 1000 kDa, such as 100 kDa to 500 kDa, such as 150 kDa to 300 kDa. In one embodiment the PEO has an average molecular weight between 100 kDa and 500 kDa. In one embodiment, the PEO has an average molecular weight between 100 kDa and 400 kDa. In one embodiment, the PEO has an average molecular weight between 100 kDa and 300 kDa. In one embodiment, the PEO has an average molecular weight of about 200 kDa.

In one embodiment, the PEO is present in the pharmaceutical composition in an amount of about 80 to 99%, such as about 85% to 95%, such as about 88% to 92%, such as about 90%. In one embodiment, the PEO is present in the composition in an amount of about 80% to 99% by weight. In one embodiment the PEO is present in the composition in an amount of about 83% to 97% by weight. In one embodiment, the PEO is present in the composition in an amount of about 85% to 95% by weight. In one embodiment the PEO is present in the composition in an amount of about 87% to 93% by weight. In one embodiment the PEO is present in the composition in an amount of about 90% by weight.

In one embodiment, the PEO is present in the pharmaceutical composition in an amount of about 85% to 95% by weight, such as 85% to 86%, such as 86% to 87%, such as 87% to 88%, such as 88% to 89%, such as 89% to 90%, such as 90% to 91%, such as 91% to 92%, such as 92% to 93%, such as 93% to 94%, such as 94% to 95% by weight.

In one embodiment according to the present disclosure, the active ingredient, the PEO and the HPMC and/or HPMC-AS are in a single matrix. In one embodiment, the composition is a uniform dispersion comprising the active ingredient, the HPMC and/or HPMC-AS and the PEO. "Uniform dispersion" means one wherein the components are evenly or homogeneous distributed through the dispersion.

PEO, HPMC and HPMC-AS are regarded as hydrophilic and gel forming. In water, a matrix made up of any of them or mixtures thereof will experience a series of processes leading to dissolution: water penetration, hydration, disentanglement, gel formation and migration of loose chains into the media.

In cases where the matrix is produced in such a way as to prevent fast penetration of water, the first step, the result is that the dosage unit is gradually eroded only forming a thin release layer on the surface. Such a matrix can be achieved by thermoplastic processes such as injection molding, hot-melt extrusion, calendering or by compression at sufficient pressures due to the high deformability/plasticity and low melting point of, in particular PEO. The object is to prevent water penetration by reducing the occurrence of cracks or inter-particular channels.

The compositions according to the present disclosure release the active ingredient predominantly by erosion. Thus, the active ingredient release closely follows the rate of erosion. This mechanism is less prone to variation between different types of active ingredient as opposed where release is mostly controlled by diffusion. The examples demonstrate that different active ingredients display comparable dissolution profiles.

One aspect of the present disclosure provides for compositions comprising a matrix comprising:

i. an active ingredient or a pharmaceutically acceptable salt thereof as described herein,
ii. HPMC and/or HPMC-AS; and
iii. polyethylene oxide (PEO), wherein the weight ratio of PEO (component i.) to HPMC and/or HPMC-AS (component ii.) is between 8:2 and 9:0.1.

In one embodiment, the PEO, the HPMC and the HPMC-AS are as described herein. In one embodiment, the weight ratio of PEO to HPMC and/or HPMC-AS is between about 8:1 and about 9.5:1, such as 8.1:1, 8.2:1, 8.3:1, 8.4:1, 8.5:1, 8.6:1, 8.7:1, 8.8:1, 8.9:1, 9.0:1, 9.1:1, 9.2:1, 9.3:1, 9.4:1 or 9.5:1.

In one embodiment, the weight ratio of PEO to HPMC and/or HPMC-AS is 9:1. In one embodiment, the weight ratio of PEO to HPMC and/or HPMC-AS is 8:2. In one embodiment, the weight ratio of PEO to HPMC and/or HPMC-AS 9.5:1. In one embodiment, the weight ratio of PEO to HPMC and/or HPMC-AS 9:0.5. In one embodiment, the weight ratio of PEO to HPMC and/or HPMC-AS 8.5:1. In one embodiment, the weight ratio of PEO to HPMC and/or HPMC-AS 8.6:1.

In one embodiment, the composition does not comprise HPMC.

Further Polymers

The composition according to the present disclosure may comprise one or more further polymers. The one or more further polymers may be independently selected from the group consisting of ionic, non-ionic, water-insoluble polymers, and water-soluble polymers. In one embodiment, the one or more polymers are one or more water-soluble polymers.

In one embodiment, the one or more further polymers are selected from the group consisting of polysaccharides, acrylates and polysiloxanes and derivatives thereof.

In another embodiment, the one or more further polymers are independently selected from the group consisting of polyethylene oxide glucomannan, galactan, glucan, polygalacturonic acid, polyhdyroxyalkanoates, polyxylane, polygalactomannans, rhanogalacturonan, polyxyloglycan, arabinogalactan, starch, alginates, xhanthan gum, carrageenan, agar, dextran, pectins, cellulose, polyvinyl alcohol, polyvinyl butyral, polyvinyl pyrrolidone, methylcellulose, ehtylcellulose, hydroxypropyl cellulose, hydroxypropyl methylcellulose stearate, carboxymethyl cellulose, carbomers, polyacrylic acid, poly(methylacrylic) acid, poly(methylmethacrylate), polyhydroxybutyrate, polyhydroxyvalerate, polyhydroxyphenylvalerate, polylactic acid, polyglycolic acid, a polyacrylic amide, and derivatives or copolymers thereof.

The inventors have surprisingly shown that the compositions according to the present disclosure do not require the presence of a lubricant. Lubricants are generally required to improve the properties of a powder during processing of formulations, and work by reducing friction. Due to the properties of PEO and the amounts of PEO used, a lubricant is not necessary during processing to prepare the compositions according to the present disclosure. Thus, in one embodiment, the composition according to the present disclosure does not comprise a lubricant. In one embodiment, the composition does not comprise and additional lubricant. For example, the composition does not comprise lubricants selected from: metallic salts of fatty acids, such as divalent salts of fatty acids, for example magnesium, calcium or zinc salts of fatty acids; fatty acids, fatty acids esters or talc.

Active Pharmaceutical Ingredient

The compositions according to the present invention provide sustained release an active ingredient or a pharmaceutically acceptable salt thereof.

The inventors have shown that the formulations according to the present disclosure provide a sustained release profile that is advantageous for active ingredients able to modulate levels of hormones or endocrine factors, especially for hormone and endocrine factors the levels of which oscillate in the human body with a period of 24 hours. Thus, in one embodiment the active ingredient is selected from the group consisting of: thyroid hormone or thyroid hormone modulators, such as triiodothyronine or triiodothyroxine; dopamine reuptake inhibitors; serotonin reuptake inhibitors; renin inhibitors; angiotensin inhibitors; angiotensin receptor antagonists; angiotensin-converting enzyme inhibitors; renin-angiotensin-aldosterone pathway inhibitors; prolactin releasers; melatonin receptor agonists, such as melatonin; corticosteroids, such as hydrocortisone, prednisolone, prednisone; follicle stimulating hormone receptor agonists; androgens, such as testosterone or testosterone derivatives; growth hormone secretagogues; ghrelin receptor agonists; fibroblast growth factor 21 analogs; fibroblast growth factor 21 receptor agonists; adiponectin receptor agonists; leptin analogs; leptin receptor agonists and vasopressin receptor agonists.

The release profile provided of the active ingredient provided by the compositions according to the present disclosure is advantageous for active ingredients that modulate hormonal or endocrine signaling of hormones or endocrine factors whose natural healthy levels increase or decrease during the night or throughout early morning and then return to baseline. In contrast to immediate-release formulations, the compositions herein disclosed allow for the administration of the active ingredient at a time that is convenient for the patient, upon which the release profile will be favorable according to the natural oscillation of the hormonal or endocrine signaling been affected.

An active ingredient may be able to modulate hormonal or endocrine signaling through different mechanisms as it will be understood by someone of skill in the art. For example, the active ingredient or salt thereof may be an endocrine factor or hormone itself, such as triiodothyronine or melatonin. The active ingredient may be a prodrug that converts into the active ingredient that is able to affect hormonal or endocrine signaling. The active ingredient may act on the same receptor in the same manner as an endogenous hormone or endocrine factor. It is also possible that the active ingredient may act in receptors upstream or downstream of the signaling pathway of a specific hormone or endocrine factor with the same effects as said hormone or endocrine factor, such as release of secondary messengers.

Thus, in one embodiment the active ingredient is able to modulate hormonal or endocrine signaling of hormones or endocrine factors whose natural healthy levels increase or decrease during the night. In one embodiment, the active ingredient modulates hormonal or endocrine signaling of which the natural levels increase or decrease between 12 am and 6 am.

In one embodiment, the natural signaling levels of said hormonal or endocrine signaling; or the natural levels of said hormone or endocrine factor increase or decrease 1 to 6 hours after the start of a major sleep episode, such as 1 to 5 hours, 1 to 4 hours, or 1 to 3 hours after the start of a major sleep episode.

In one embodiment the active ingredient is able to modulate hormonal or endocrine signaling of hormones or endocrine factors whose natural healthy levels increase or decrease throughout early morning.

For example signaling of hormones and endocrine factors such as thyroid hormones, melatonin, prolactin, ghrelin, leptin or vasopressin increase during the night ours[12]. Thus, in one embodiment, the active ingredient is selected from the group consisting of: thyroid hormones, melatonin receptor agonists, prolactin releasers, ghrelin receptor agonists, leptin receptor agonists and vasopressin receptor agonists.

Signaling of hormones and endocrine factors such as cortisol, testosterone, fibroblast growth factor or adiponectin increase through early morning. Thus, in one embodiment, the active ingredient is selected from the group consisting of: corticosteroids, androgens, fibroblast growth factor 21 analogues and adiponectin receptor agonists.

The renin-angiotensin-aldosterone system is a key regulator of blood pressure, mainly by production of angiotensin II. Renin secretion is activated in the early morning before arousal as a result of sympathetic neuronal activation. Both renin and aldosterone demonstrate significant circadian patterns in both normotensive and hypertensive individuals, with peak values detected early morning, then falling to their lowest point in late evening. Therefore, renin-angiotensin inhibitors can be administered to lower the signalling and thereby blood pressure in hypertension patients. In one embodiment, the active ingredient is selected from the group consisting of: renin inhibitors, angiotensin inhibitors, angiotensin receptor antagonists, angiotensin-converting enzyme inhibitors and renin-angiotensin-aldosterone pathway inhibitors.

As demonstrated by the examples, the formulations according to the present disclosure provide sustained release of the active ingredient that is adequate to match the natural oscillation of levels of different hormones or endocrine factors during the 24-hour period in healthy individuals with safe return to baseline. Thus, the formulations according to the present disclosure have great potential to provide the active ingredient according to the patients' needs, leading to better therapeutic outcomes, reduction of side-effects and/or improved quality of life—specially for patients requiring chronic treatments.

In one embodiment, the present disclosure provides for a composition comprising:

a. an active ingredient or a pharmaceutically acceptable salt thereof, as described herein, b. hydroxypropyl methyl cellulose acetate succinate (HPMC-AS) and/or hydroxypropyl methyl cellulose (HPMC) in a total amount of 0.1% to 20% by weight, as described herein and
c. polyethylene oxide (PEO) in an amount from 80 to 99.9% by weight.

In one embodiment, the present disclosure provides for a composition comprising:
a. an active ingredient or a pharmaceutically acceptable salt thereof, as described herein,
b. hydroxypropyl methyl cellulose acetate succinate (HPMC-AS) in an amount of 0.1% to 20% by weight, as described herein and
c. polyethylene oxide (PEO) in an amount from 80 to 99.9% by weight.

In one embodiment, the present disclosure provides for a composition comprising:
a. an active ingredient or a pharmaceutically acceptable salt thereof, as described herein,
b. hydroxypropyl methyl cellulose (HPMC) in an amount of 0.1% to 20% by weight, as described herein and
c. polyethylene oxide (PEO) in an amount from 80 to 99.9% by weight.

In one embodiment, the active ingredient is a thyroid hormone, for example triiodithyronine or triiodothyroxine.

In one embodiment, the active ingredient is triiodothyroxine (also referred to herein as: T4, or thyroxine) or a pharmaceutically acceptable salt thereof.

In one embodiment, the active ingredient is triiodothyronine (also referred to herein as: T3, LT3 or liothyronine) or a pharmaceutically acceptable salt thereof.

Triiodothyronine is not stable in the pH and enzymatic conditions in the stomach. Thus, one advantage of the sustained release compositions according to the present disclosure is the at least partial protection of T3 from degradation in the stomach, thus allowing for higher bioavailability compared to immediate release formulations.

In one embodiment, the composition according to the present invention comprises triiodothyronine or a pharmaceutically acceptable salt thereof in an amount between 1 and 100 μg, such as between about 2 and 70 μg, for example between about 5 and 50 μg.

In one embodiment, the composition according to the present invention comprises triiodothyronine or a pharmaceutically acceptable salt thereof in an amount between 5 and 50 μg, such as 5 to 7 μg, such as 7 to 9 μg, such as 9 to 11 μg, such as 11 to 13 μg, such as 13 to 15 μg, such as 15 to 17 μg, such as 19 to 21 μg, such as 21 to 23 μg, such as 23 to 25 μg, such as 25 to 27 μg, such as 27 to 29 μg, such as 29 to 31 μg, such as 31 to 33 μg, such as 33 to 35 μg, such as 35 to 37 μg, such as 37 to 39 μg, such as 39 to 41 μg, such as 41 to 43 μg, such as 43 to 45 μg, such as 45 to 47 μg, such as 47 to 50 μg.

In one embodiment, the present disclosure provides for a composition comprising:
a. triiodothyronine or a pharmaceutically acceptable salt thereof, as described herein,
b. hydroxypropyl methyl cellulose acetate succinate (HPMC-AS) and/or hydroxypropyl methyl cellulose (HPMC) in a total amount of 0.1% to 20% by weight, as described herein and
c. polyethylene oxide (PEO) in an amount from 80 to 99.9% by weight.

In one embodiment, the active ingredient is a corticosteroid or a pharmaceutically acceptable salt thereof, such as hydrocortisone, prednisolone, prednisone.

In one embodiment, the present disclosure provides for a composition comprising:
a. a corticosteroid or a pharmaceutically acceptable salt thereof, as described herein,
b. hydroxypropyl methyl cellulose acetate succinate (HPMC-AS) and/or hydroxypropyl methyl cellulose (HPMC) in a total amount of 0.1% to 20% by weight, as described herein and
c. polyethylene oxide (PEO) in an amount from 80 to 99.9% by weight.

In one embodiment, the active ingredient is a dopamine reuptake inhibitor or a pharmaceutically acceptable salt thereof, such as bupropion, wellbutrin, forfivo or aplezin.

In one embodiment, the present disclosure provides for a compositions comprising:
a. dopamine reuptake inhibitor or a pharmaceutically acceptable salt thereof, as described herein,
b. hydroxypropyl methyl cellulose acetate succinate (HPMC-AS) and/or hydroxypropyl methyl cellulose (HPMC) in a total amount of 0.1% to 20% by weight, as described herein and
c. polyethylene oxide (PEO) in an amount from 80 to 99.9% by weight.

In one embodiment, the active ingredient is a serotonin reuptake inhibitor or a pharmaceutically acceptable salt thereof, such as sertraline, fluoxetine, citalopram, escitalopram, paroxetine or fluvoxamine.

In one embodiment, the present disclosure provides for a composition comprising:
a. a serotonin reuptake inhibitor or a pharmaceutically acceptable salt thereof, as described herein,
b. hydroxypropyl methyl cellulose acetate succinate (HPMC-AS) and/or hydroxypropyl methyl cellulose (HPMC) in a total amount of 0.1% to 20% by weight, as described herein and
c. polyethylene oxide (PEO) in an amount from 80 to 99.9% by weight.

In one embodiment, the active ingredient is a melatonin receptor agonist or a pharmaceutically acceptable salt thereof, such as melatonin.

In one embodiment, the present disclosure provides for a composition comprising:
a. a melatonin receptor agonist or a pharmaceutically acceptable salt thereof, as described herein,
b. hydroxypropyl methyl cellulose acetate succinate (HPMC-AS) and/or hydroxypropyl methyl cellulose (HPMC) in a total amount of 0.1% to 20% by weight, as described herein and
c. polyethylene oxide (PEO) in an amount from 80 to 99.9% by weight.

In one embodiment, the active ingredient is melatonin or a pharmaceutically acceptable salt thereof.

In one embodiment, the active ingredient is a renin inhibitor or a pharmaceutically acceptable salt thereof able to lower blood pressure, such as aliskiren. In one embodiment, the active ingredient is an angiotensin inhibitor, an angiotensin receptor blocker or an angiotensin-converting enzyme inhibitor or a pharmaceutically acceptable salt thereof able to lower blood pressure. In one embodiment, the active ingredient is a renin-angiotensin-aldosterone pathway inhibitor or a pharmaceutically acceptable salt thereof.

In one embodiment, the present disclosure provides for a composition comprising:
a. a renin inhibitor or a angiotensin inhibitor or a pharmaceutically acceptable salt thereof, as described herein, b. hydroxypropyl methyl cellulose acetate succinate (HPMC-AS) and/or hydroxypropyl methyl cellulose (HPMC) in a total amount of 0.1% to 20% by weight, as described herein and c. polyethylene oxide (PEO) in an amount from 80 to 99.9% by weight.

In one embodiment, the active ingredient is a prolactin releaser or a pharmaceutically acceptable salt thereof able to induce secretion of prolactin.

In one embodiment, the present disclosure provides for a composition comprising:

a. a prolactin releaser or a pharmaceutically acceptable salt thereof, as described herein, b. hydroxypropyl methyl cellulose acetate succinate (HPMC-AS) and/or hydroxypropyl methyl cellulose (HPMC) in a total amount of 0.1% to 20% by weight, as described herein and c. polyethylene oxide (PEO) in an amount from 80 to 99.9% by weight.

A Method of Preparation

One aspect of the present disclosure provides for a method of manufacturing a composition comprising the steps of:

a. preparing a melt uniform dispersion comprising i) PEO, ii) hydroxypropyl methyl cellulose and/or HPMC-AS and iii) an active ingredient or a pharmaceutically acceptable salt thereof, and b. cooling the melt to obtain a solid composition.

A melt can be prepared by heating a mixture of powders to a temperature at least partially melting the powders, or one of the powders. In one embodiment, step a) comprises heating the mixture to a temperature at least partially melting the powders, or one of the powders. In one embodiment, step a) further comprises compressing the mixture.

In one aspect, the present disclosure provides for a method of manufacturing a composition comprising the steps of:

i. mixing powders of an active ingredient or a pharmaceutically acceptable salt thereof, HPMC and/or HPMC-AS and PEO, ii. compacting the mixture to obtain uniform dispersion of components in a matrix.

The processes and methodologies to achieve uniform dispersions either through a melt dispersion or through mixing and compacting solids are well known to a person of skill in the art[14]. For example methodologies to implement the methods herein described include but are not limited to: dry granulation such as achieved by roller compaction, calendering, slugging or pneumatic dry granulation; compression moulding, such as vacuum compression moulding (VCM); direct compression (DCT); hot melt extrusion (HME); ultrasound assisted compaction; or wet granulation.

In one embodiment, step i) of compacting the mixture to obtain a uniform dispersion of components in a matrix is performed by dry granulation methods. In one embodiment, the dry granulation is performed by roller compaction.

In one embodiment, the method further comprises a step of compressing the composition into a solid composition. In one embodiment, the composition is pressed into a tablet.

Thus, in one embodiment the composition according to the present disclosure is compressed into a tablet. Compressing with sufficient force provides for tablets wherein the fissures between the granules are small and this reduces the rate of water penetration, ensuring proper erosion of the tablet. A person of skill in the art is aware on how to achieve proper compression to ensure slow rate of water penetration and how to optimize the force of compression according to the materials or equipment used.

In one embodiment, the PEO, the HPMC and or HPMC-AS and the active ingredient are as described herein.

Excipients

The composition according to the present disclosure may comprise one or more additional excipients. An excipient is a pharmacologically inactive substance formulated with the active ingredient of a medication.

In one embodiment, the pharmaceutical composition according to the present invention comprises one or more excipients. Said one or more excipients may act as a solid carrier, diluent, flavouring agent, solubilizer, lubricant, glidant, suspending agent, binder, filler, preservative, antiadherent, wetting agent, tablet disintegrating agent, sorbent, and/or an encapsulating/coating material.

In one embodiment, the one or more additional excipients are selected from one or more of the groups consisting of: binders, fillers, lubricants, release-controlling excipients, stabilizers, plasticizers, antioxidants and preservatives.

In one embodiment, the composition comprises a filler, such as a filler selected from the group consisting of calcium carbonate, calcium phosphates, calcium sulfate, cellulose, cellulose acetate, compressible sugar, dextrate, dextrin, dextrose, ethylcellulose, fructose, isomalt, lactitol, lactose, mannitol, magnesium carbonate, magnesium oxide, maltodextrin, microcrystalline cellulose (MCC), polydextrose, sodium alginate, sorbitol, talc and xylitol.

In one embodiment, the composition comprises a binder, such as a binder selected from the group consisting of acacia, alginic acid, carbomers, carboxymethylcellulose sodium, carrageenan, cellulose acetate phthalate, chitosan, copovidone, dextrate, dextrin, dextrose, ethylcellulose, gelatin, guar gum, hydroyethyl cellulose, hydroxyethylmethyl cellulose, hydroxypropyl cellulose, hydroxypropyl starch, hypromellose, methylcellulose, poloxamer, polydextrose, polyethylene oxide, povidone, sodium alginate, sucrose, starch, pregelatinized starch and maltodextrin.

In one embodiment, the composition comprises a lubricant, such as a lubricant selected from the group consisting of calcium stearate, glycerin monostearate, glyceryl behenate, glyceryl palmitostearate, hydrogenated castor oil, hydrogenated vegetable oil, magnesium lauryl sulfate, magnesium stearate, medium chain triglyceride, palmitic acid, polyethylene glycol, sodium lauryl sulfate, stearic acid, talc, silica and zinc stearate.

A preservative may be an antimicrobial or an antioxidant. A preservative may also be a light filter or a light blocker, such as $TiO_2$. In one embodiment of the present disclosure, the composition comprises one or more preservatives. In one embodiment the one or more preservatives are independently selected form the group consisting of: antimicrobials, antioxidants, a light filter or a light blocker.

In one embodiment, the composition comprises a release-controlling excipient, such as a release controlling excipient selected from the group consisting of functionalized celluloses, glycerin monostearate, glyceryl monooleate, glyceryl palmitate, glyceryl behenate, hydrogenated vegetable oil, guar gum, polyvinyl alcohol, alginates, xanthan gum, carnauba wax, yellow wax, white wax, zein, carregeenan, carbomers and agar.

Any other excipients suitable for the purpose of the present invention and known to the skilled person are considered encompassed by the present invention.

Sustained Release Formulation

Tablet

In one embodiment, the present disclosure relates to pharmaceutical formulations or pharmaceutical compositions comprising the compositions described herein.

Thus in one embodiment, the composition as described herein is a pharmaceutical composition. In one embodiment, the composition as described herein is a pharmaceutical formulation.

The terms pharmaceutical formulation, pharmaceutically safe formulation and pharmaceutically acceptable formulation are used interchangeably.

In one embodiment, the pharmaceutical formulation or the pharmaceutical compositions described herein provide sustained release of triiodothyronine or a pharmaceutically acceptable salt thereof.

A tablet is a pharmaceutical dosage form comprising a mixture of (an) active substance(s) and excipients, pressed or compacted into a solid dose. Tablets are simple and convenient to use. They provide an accurately measured dosage of the active ingredient(s) in a convenient portable package. Manufacturing processes and techniques can provide tablets special properties, for example, extended release or fast dissolving formulations. Tablets are easy to weigh out and have high physical integrity.

Tablets can be manufactured by methods known in the art, for example but not limited to: vacuum compression moulding (VCM), wet granulation, dry granulation, direct compression (DCT), hot melt extrusion and calendering, roller compaction or combinations thereof. In one embodiment, the tablet is prepared as described herein.

In one embodiment the pharmaceutical formulation is selected from the group consisting of a tablet, a mini-tablet a micro-tablet, a coated tablet, a coated mini-tablet, a coated micro-tablet, a sphere and a coated sphere.

In one embodiment the pharmaceutical formulation is a monolithical dosage form, such as for example a cylindrical monolithical tablet.

In one embodiment the pharmaceutical formulation is a tablet with a total weight of 50 to 800 mg.

In one embodiment the pharmaceutical formulation is a tablet with a total weight of 50 to 250 mg, such as 100 to 200 mg, such as 150 mg.

In another embodiment, the tablet has a volume/weight ratio between 100 and 200, such as 130 to 170, for example 140 to 160, such as 150.

In one embodiment, the pharmaceutical formulation is a cylindrical tablet wherein the tablet has one dimension measuring 2 to 4 mm, such as 3 mm and another measuring 6 to 20 mm, such as 8 mm.

According to the present disclosure, the pharmaceutical formulation may comprise a coating. A coating may be formed by materials such that it provides protection and stabilization of the formulation. The coating may comprise further excipients as described herein.

Thus, in one embodiment the pharmaceutical formulation further comprises a coating. In a further embodiment, the coating material comprises one or more polymers. In another embodiment, the coating material comprises one or more of the group consisting of polyacrylates, polyacrylate derivatives and copolymers thereof. In another embodiment, the coating material comprises one or more cellulose derivatives. In another embodiment, the coating material comprises shellac.

In one embodiment the pharmaceutical formulation is orally available.

In one embodiment the pharmaceutical formulation is a solid dosage form. In one embodiment said formulation is an orally available solid dosage form.

In one embodiment the pharmaceutical formulation is a single-unit oral dosage form. In another embodiment, the pharmaceutical formulation is a multiple-unit oral dosage form.

In one embodiment, the formulation unit is selected from the group consisting of a coated or un-coated tablet, a coated or un-coated mini tablet, a coated or uncoated micro-tablet and a coated or uncoated sphere or a thermoformed solid oral dosage form.

In one embodiment, the pharmaceutical formulation is contained within a capsule, such as a hard shell capsule, such as a hard-shelled capsule further comprising an outer coating.

In a sustained release composition multiple factors will potentially impact the release rates of the active ingredient. The release rates may be determined by evaluating the dissolution profiles of the produced batches. In vitro drug dissolution data generated from dissolution testing experiments can be related to in vivo pharmacokinetic data by means of in vitro-in vivo correlations (IVIVC).

Medical Use

In one aspect, the present disclosure relates to a composition or a pharmaceutical formulation as described herein for use as a medicament.

In one aspect, the present disclosure relates to a composition or a pharmaceutical formulation as described herein for use in the modulation able to modulate hormonal or endocrine signaling.

In one embodiment, the natural levels of the hormonal or endocrine signalling oscillate during the 24 hour period. In one embodiment, the natural levels of the hormonal or endocrine signalling increase or decrease between 12 am and 7 am.

In one embodiment the present disclosure relates to compositions or pharmaceutical formulations as described herein for use in the treatment of hypothyroidism and/or for use to prevent or reduce the appearance of side effects associated with hypothyroidism treatments.

In one embodiment the present disclosure relates to compositions or pharmaceutical formulations as described herein for use in the treatment of bone damage, cartilage damage, myxedema, goiter, and/or in the treatment stroke.

Hypothyroidism may originate from multiple causes, for example an autoimmune disease, radiation treatment, surgical removal of part or all of the thyroid gland, treatment with other medications, congenital disease or pregnancy. It may also appear in patients suffering from cancer or it may be caused by treatment with other medications, then it is known as drug-induced hypothyroidism.

Thus, in one embodiment the present disclosure relates to a composition or pharmaceutical formulation for use in the treatment of hypothyroidism, wherein the hypothyroidism is caused by one or more selected from the group consisting of: an autoimmune disease, radiation treatment, surgical removal of part or all of the thyroid gland (thyroidectomy), treatment with other medications, congenital disease and pregnancy.

In one embodiment, the present disclosure relates to a composition or pharmaceutical formulation for use in the treatment of hypothyroidism, wherein said hypothyroidism is drug-induced hypothyroidism.

In one embodiment, the present disclosure relates to a composition or pharmaceutical formulation for use in in the treatment of hypothyroidism in a generic cancer patient displaying low levels of thyroid hormone. In another embodiment, said cancer patient is treated with checkpoint inhibitors. In a further embodiment, said checkpoint inhibitors are selected from the group consisting of CTLA-4 and/or a-PDL1.

One advantage of the invention disclosed herein is providing physiological hormone levels according to natural oscillation with the circadian rhythm and a safe return to baseline levels.

In one embodiment, the present disclosure relates to a composition or pharmaceutical formulation for use in reducing and/or preventing a side effect of hypothyroidism treatment. In another embodiment, said side effect is one or more selected from the group consisting of cardiovascular diseases, hypertension, mineral metabolism complications, depression, trouble breathing, headache, tremors, feeling nervous or irritable, muscle weakness, increased appetite, diarrhoea, irregular menstrual periods, weight loss, feeling hot, rash and sleep disorders.

In one embodiment, the pharmaceutical composition or the pharmaceutical formulation described herein is to be administered to a patient suffering from a side effect of hypothyroidism treatment.

In one embodiment, the present disclosure relates to a composition or pharmaceutical formulation as described herein for use in treatment or prevention of neuro-degenerative diseases, such as Alzheimer's or Huntington's disease.

In one embodiment, the present disclosure relates to a composition or pharmaceutical formulation as described herein for use in stimulation and maturation of chondrocytes and the progression of endochondral ossification during fractures or damage to cartilage. In one embodiment, the present disclosure relates to a composition or pharmaceutical formulation as described herein for use in the treatment of stroke in the postischemic brain injury or accidents.

In one embodiment, the present disclosure relates to a composition or pharmaceutical formulation as described herein for use in underweight patients, wherein the composition or formulation comprises between 10 and 75 µg of triiodothyronine or a pharmaceutically acceptable salt thereof.

In one embodiment, the present disclosure relates to a composition or pharmaceutical formulation wherein the composition or formulation comprises between 2.5 and 25 µg of triiodothyronine or a pharmaceutically acceptable salt thereof, for use in as described herein in children below 18 years of age, underweight patients or patients needing to be dosed more than once.

Administration Times and Parameters

In one embodiment, the composition or the pharmaceutical formulation described herein is to be administered between 18 h and 00 h, such as between 20 h and 22 h, for example at 21 h.

In one embodiment, the composition or the pharmaceutical formulation described herein is to be administered during dinner or after dinner, such as within 3 hours after dinner, such as within 2 hours after dinner, such as within 1 hour after dinner, such as within 30 minutes after dinner.

In one embodiment, the composition or the pharmaceutical formulation described herein is to be administered prior to a major sleep episode such as within 3 hours before a major sleep episode, such as within 2 hours before a major sleep episode, for example within 1 hour before a major sleep episode, such as within 30 minutes before a major sleep episode.

In one embodiment, the composition or the pharmaceutical formulation described herein is to be administered once daily.

In one embodiment, the composition or the pharmaceutical formulation described herein is administered more than once daily.

In one embodiment, the composition or the pharmaceutical formulation described herein is administered on an empty stomach.

In one embodiment, the composition or the pharmaceutical formulation described herein provides an increase in $T_{max}$ of triiodothyronine, as compared to an equivalent amount of triiodothyronine administered as an immediate release formulation.

In one embodiment, said increase in $T_{max}$ is of at least about 1 hour, such as at least about 2 hours, for example at least about 3 hours, such as at least about 4 hours, for example at least about 6 hours as compared to an equivalent amount of triiodothyronine administered as an immediate release formulation.

In one embodiment, the composition or the pharmaceutical formulation described herein provides a $c_{max}$ of triiodothyronine between 150 and 400 ng/dL, such as between 200 and 350 ng/dL.

EXAMPLES

Example 1: Formulation Manufacturing

Aim

To illustrate the preparation of sustained release formulations.

Materials and Methods

Formulations with Ibuprofen as T3 Substitute:

Formulations A, B, C, E and F were prepared as detailed below:

Methocel™ (HydroxyPropyl MethylCellulose, HPMC, Methocel K100M) or Aqoat® (hydroxypropyl methylcellulose acetate succinate, HPMC_AS, Aqoat-AS-LF) were mixed with PolyEthylene Oxide, (PEO Polyox™ NF80 of molecular weight 200 kDa.

5 mg of ibuprofen (Sigma-Aldrich) was mixed homogenously with PEO (molecular weight 200 kDa) alone or with 5-10% Methocel™ or 5-10% Aqoat® and formed into tablets by using a vacuum melt extruder (MeltPrep® VCM). The size of the cylindrical tablet was 8 mm in diameter and 3 mm in height, (Volume/weight=11) with total tablet weight of 150 mg.

Formulation with T3:

Formulations D, G, H and I were prepared as detailed below:

Aqoat® (hydroxypropyl methylcellulose acetate succinate, HPMC-AS) was mixed with PEO of molecular weight 200 kDa.

T3 as an API was bought from T3 TOCRIS (Cat. No. 6666). For formulation D, 50 µg of T3 were mixed homogenously using aliquot dilution to ensure homogeneity with PEO of molecular weight 200 kDa with 10% Aqoat using vacuum melt extruder (MeltPrep® VCM). The size of the cylindrical tablet (8 mm in diameter) and (3 mm in height), (Volume/weight=1) with total tablet weight of 150 mg.

Formulations G, H and I were prepared by dry granulation method using roller compaction. Three different amounts of T3 were used (40 µg, 30 µg and 20 µg) with varying total weight of matrix and amount of HPMC-AS as described in table 1.

TABLE 1

Formulations prepared.

| ID | Method | [c]Size, weight | API (mg) [d]Ibu | API (mg) T3 | Matrix components (mg) PEO | Methocel ™ | Aqoat ® |
|---|---|---|---|---|---|---|---|
| A | VCM | 3 × 8, 150 mg | 5 | — | 145 | — | — |
| B | VCM | 3 × 8, 150 mg | 5 | — | 130 | 15 | — |
| C | VCM | 3 × 8, 150 mg | 5 | — | 130 | — | 15 |
| D | VCM | 3 × 8, 150 mg | — | 0.05 | 135 | — | 15 |
| E | VCM | 3 × 8, 150 mg | 5 | — | 137.5 | 7.5 | — |
| F | VCM | 3 × 8, 150 mg | 5 | — | 137.5 | — | 7.5 |
| G | DGRC | 2 × 8, 100 mg | — | 0.02 | 90 | — | 10 |
| H | DGRC | 3 × 8, 150 mg | — | 0.03 | 135 | — | 15 |
| I | DGRC | 4 × 8, 200 mg | — | 0.04 | 180 | — | 20 |

[a]VCM: Vacuum Compression Moulding using MeltPrep ®.
[b]DGRC—dry granulation using roller compaction.
[c]Size and weight: cylindrical size mm height × mm diameter, weight in mg.
[d]Ibuprofen Example 2: Dissolution Experiments on T3 Substitute Aim To study the dissolution profile of the sustained release formulations with an API analog.

Materials and Method

Dissolution Method:

Experiments were performed to measure the cumulative drug release in % as a function of time for using ibuprofen as T3 substitute.

The dissolution experiment was conducted in a USP Apparatus 2 with special inserts and 250-mL vessels (Erweka DT 70, Heusenstamm, Germany). Tablets are studied in duplicate (n=2). Prepare 2 liters of 0.1 M phosphate buffer pH 6.8 Preheat the USP bath 250 ml 0.1 M phosphate buffer pH 6.8 is added to each of the six dissolution vessels. The vessels are then allowed to reach 37 degrees (15 min). FaSSGF media (was added to the beakers and simulated intestinal fluid and pH6.8 with phosphate buffer simulated intestinal fluid. The dissolution experiments were conducted at 37±0.1° C. paddle stirring rate of 50 rpm for up to 24 hrs at pH6.8 (2 of each formulation). Samples (1 mL) were removed at time 0.5, 1, 1.5, 2, 2.5, 3, 3.5, 4, 4.5 and 5 hours a sample of 0.5 ml is taken from each vessel and placed directly in a HPLC vial. After 24 h a sample is also taken and analyzed, and the experiment is terminated. After the experiment is terminated the samples are run untreated in HPLCA standard curve from 250-1 ug/ml is also prepared in triplicate A high-performance liquid chromatograph (HPLC) method was used for quantification of ibuprofen using an Ultimate 3000 HPLC system from Dionex (Sunnyvale, USA). A reverse phase Kinetex 100A XB-C18 column (4.6×100 mm, 5 µm) from Phenomenex (Vmrløse, Denmark) was used for the separation and the mobile phase consisted of A) 0.1% acetic acid and B) 0.1% acetic acid in acetonitrile. A gradient of solvent B was continuously mixed with solvent A in the following sequence: 0 min 50% B, 2 min 80% B, 3 min 100% B, 7 min 55% B, 10 min 50% B. A volume of 10 µl was eluted at a flow rate of 1.0 ml/min, and the effluent was detected at a wavelength of 230 nm after approximately 2.9 min. The concentrations of ibuprofen were then calculated using the mean value of the peak areas obtained from the standard curve. The standard curve was linear over the range 1-250 µg/ml.

Results

The results show that formulations A, B, C, E and F have delayed drug release of ibuprofen as T3 substitute (FIG. 1). The dissolution profiles of formulations A, B, C, E and F are delayed when compared to published values from immediate release liothyronine products such as described in Bowerbank et al. 2019[9] and in U.S. Pat. No. 9,526,701. Formulation A showing dissolution profile delayed 1-2 hours and formulations B, C, E and F dissolution profile delayed 3-4 hours compared to immediate release liothyronine products.

Conclusion

Formulations according to the present disclosure have delayed drug release compared to existing immediate release liothyronine formulations.

Example 3: IVIVC Correlations of T3 Substitute

Aim

To demonstrate the ability of the formulations according to provide sustained release matching the natural variation of hormone levels.

Method

The in vitro in vivo correlation (IVIVC) method uses in vitro dissolution data to derive blood drug levels using pharmacokinetic parameters of a test product. The convolution approach starts with dissolution results or profiles and develops the in vivo or drug concentration-time estimated profiles. Thus, using the dissolution rate data obtained for formulation A-C with T3 substitute ibuprofen, the expected profiles of T3 at different dosages were modelled using a well validated method as described in Qureshi et al. 2010[10]. Briefly, these profiles are converted into discrete dosage segments. The bioavailability is 95% for T3, Half-life (t½) is estimated to be 4 h after baseline (120 ng/dL) correction, Volume of distribution (Vd) is 0.2 L/kg for body weight (BW) of 75 kg euthyroid individual. Then different pharmacokinetic parameters were calculated.

Results

Figure 2:
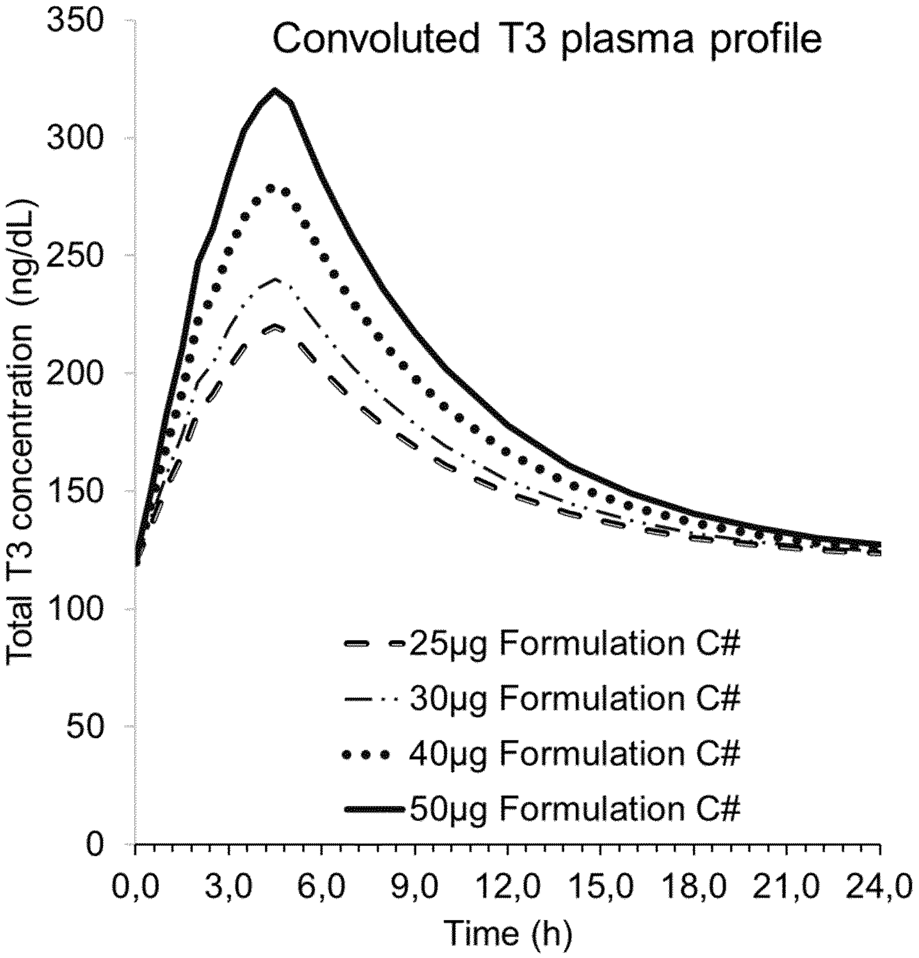
FIG. 2. Predicted T3 plasma profiles at different dosages of T3 obtained by in vitro-in vivo correlation (IVIVC) based on the dissolution rate of T3 model compound in formulation C.

The convoluted predicted total T3 serum plasma profiles (IVIC) for Formulation C at different T3 doses are shown in FIG. 2. Different predicted pharmacokinetic parameters for formulations A-C assuming a dose of T3 of 50 µg are shown in Table 2.

The predicted values from the IVIVC correlation denote display delayed release and return to baseline after 24 hrs. This is in contrast with published data from immediate release in Bowerbank et al. 2019[9] and in U.S. Pat. No. 9,526,701. Moreover, the predicted values are in accordance with desired physiological values of T3 and day/night cycle variations.

TABLE 2

Pharmacokinetic (PK) parameters estimated from IVIVC correlations based on dissolution profiles of Formulations A-C, E and F with T3 substitute ibuprofen.

| | Formulation | | | | |
|---|---|---|---|---|---|
| PK parameter | A | B | C | E | F |
| Total T3[a] (mg) | 0.05 | 0.05 | 0.05 | 0.05 | 0.05 |
| Baseline T3 (ng/dL) | 120 | 120 | 120 | 120 | 120 |
| Cmax (ng/dL) | 343 | 324 | 320 | 322.3162 | 322.4284 |
| Tmax (hours) | 3 | 4 | 4.5 | 4.5 | 4 |
| AUC 0-24 hours (ng*h/dL) | 4706 | 4374 | 4612 | 4633.412 | 4651.843 |

[a]Assumed dose of T3.

Results

Figure 3:
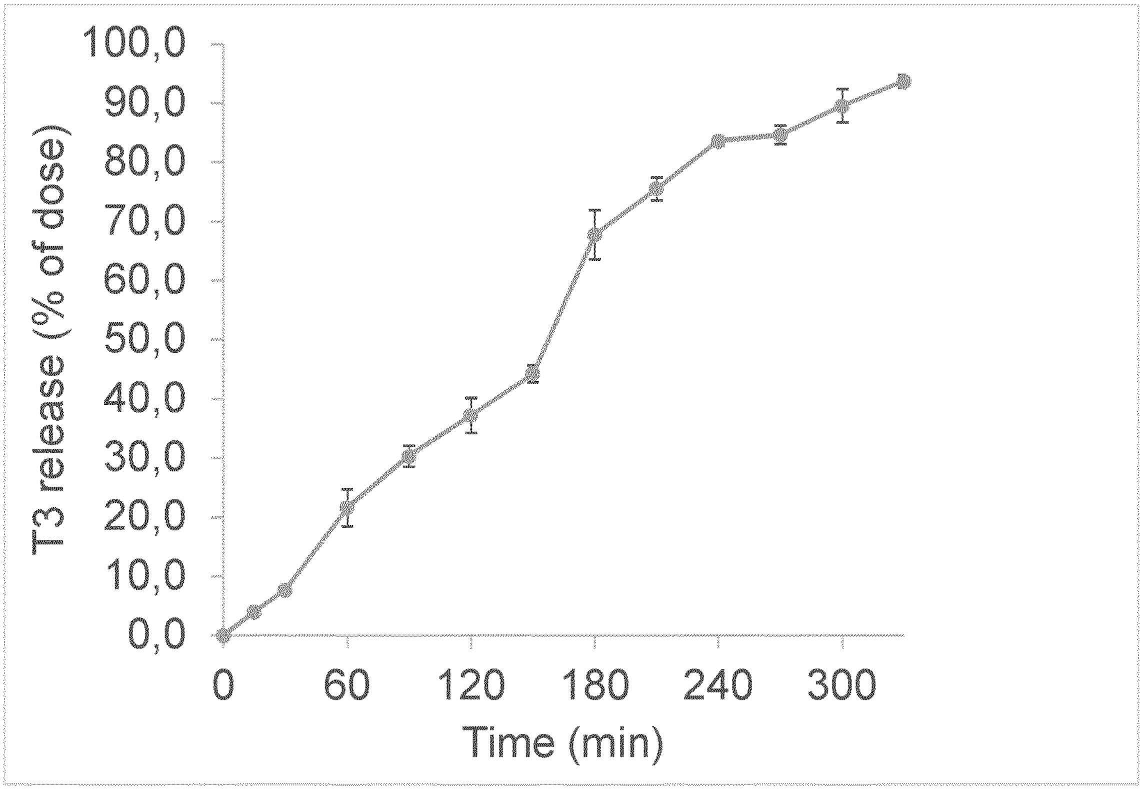
FIG. 3. Dissolution profiles of 50 μg T3 in formulation D in two tablets analysed by ELISA.

The results show that formulation D has delayed drug release of T3 (FIG. 3). Dissolution rates are comparable to observations made in formulation C with T3 substitute.

Figure 4:
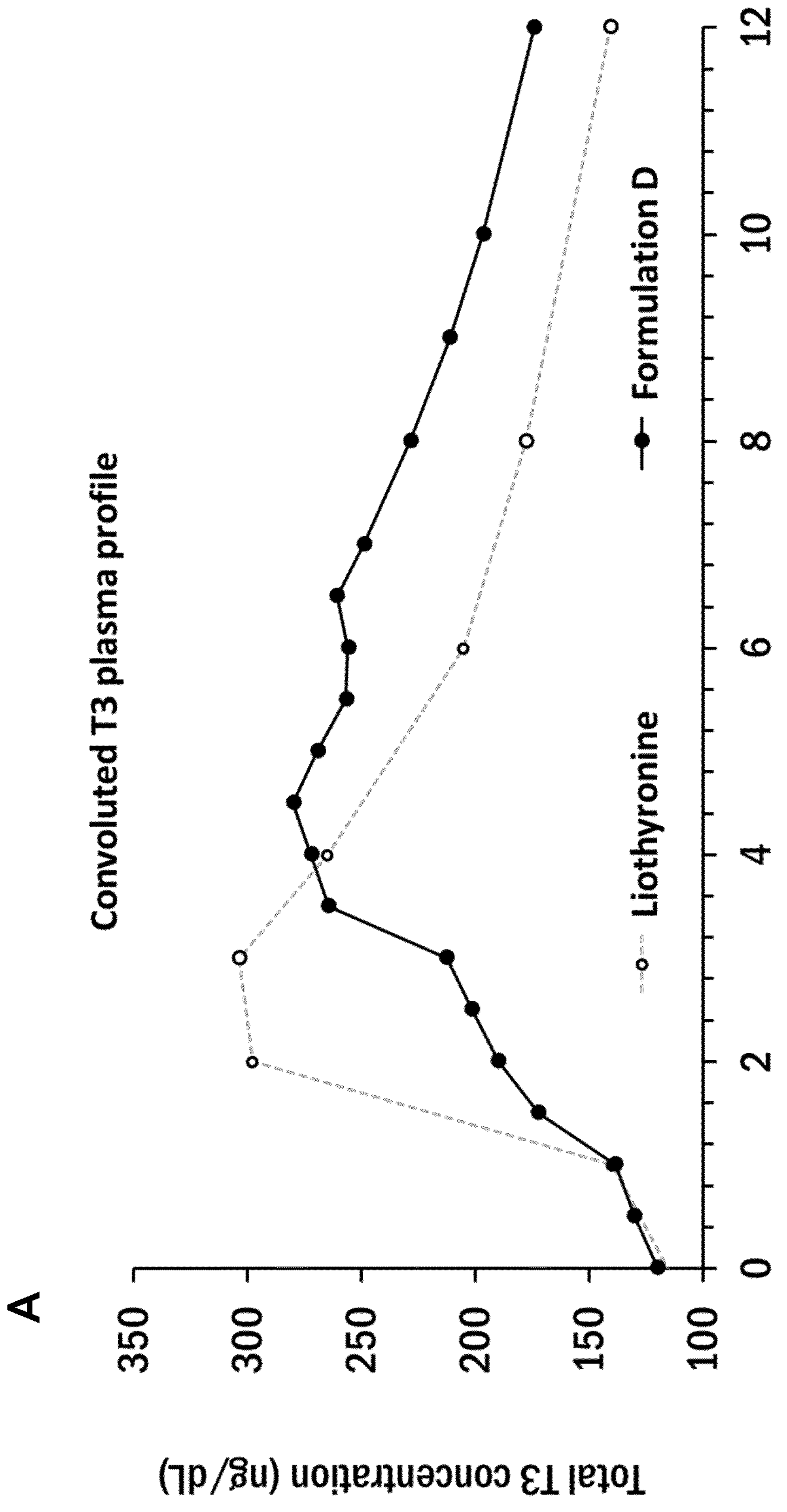
FIG. 4. A Convoluted average T3 plasma profiles (with 120 ng/dL estimated baseline) 40 μg T3 formulation D (n=3, quantified through ELISA) compared to 50 μg generic Liothyronine (T3 immediate release, experimental in vivo profile[13]). Convolution method was adopted from Qureshi et al. 2010[10]. B Dissolution profiles of T3 tablets of formulations G, H and I manufactured with dry granulation using roller compaction, analyzed by ELISA. C Convoluted IVIVC T3 plasma profiles (with 120 ng/dL estimated baseline) for tablets of formulations G, H and I. D Convoluted average T3 plasma profiles (with 120 ng/dL estimated baseline) depict delayed release of assumed 20 μg, 30 μg, 40 and 50 μg T3 with 200 mg tablet (Formulation I). E Convoluted average T3 plasma profiles (with 120 ng/dL estimated baseline) depict delayed release of assumed 20 μg, 30 μg, 40 and 50 μg T3 with 150 mg tablet (Formulation H). F Convoluted average T3 plasma profiles (with 120 ng/dL estimated baseline) depict delayed release of assumed 20 μg, 30 μg, 40 and 50 μg T3 with 100 mg tablet (Formulation G).

The predicted values from the IVIVC correlation display a delayed release profile and return to baseline after 24 hrs in accordance to the desired physiological values of T3 and day/night cycle variations (FIG. 4A).

Figure 6:
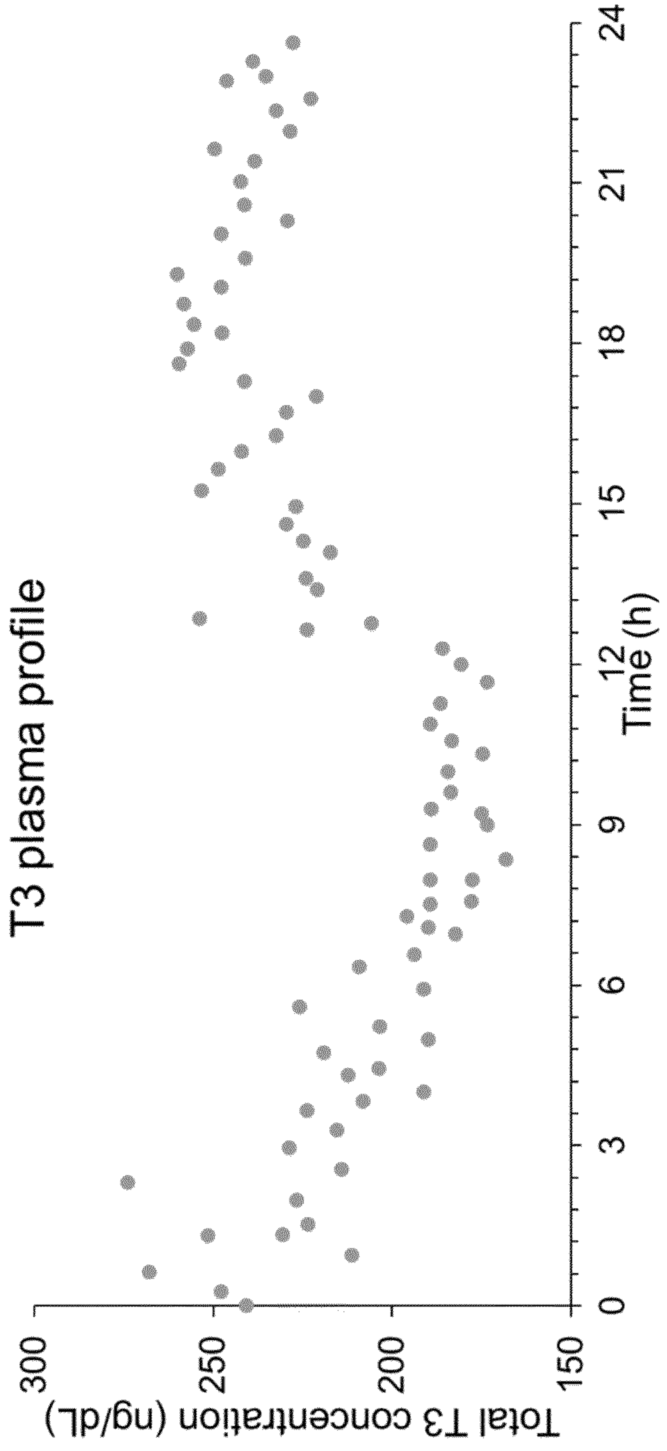
FIG. 6. Oscillation of T3 levels during a 24 hour period, the time axis in the graph represents from 9 am (time=0). The results are adapted from *J Clin Endocrinol Metab* 93: 2300-2306, 20084.

When varying the dose of T3, different tablets adjusting the amount of matrix (Formulations G, H and I) display adequate dissolution profiles as shown in FIG. 4B. The IVIVC correlations shown in FIGS. 4C-4F confirm delayed release profile and return to baseline after 24 hrs in accordance to the desired physiological values of T3 and day/night cycle variations (depicted in FIG. 6).

TABLE 3

Pharmacokinetic (PK) parameters estimated from IVIVC correlations based on dissolution profiles of Formulations D and G-I with T3.

| | Formulation | | | |
|---|---|---|---|---|
| PK parameter | D | G | H | I |
| Total T3[a] (mg) | 0.05 | 0.02 | 0.03 | 0.04 |
| Baseline T3 (ng/dL) | 120 | 120 | 120 | 120 |
| Cmax (ng/dL) | 352.6535 | 206.8483 | 239.7379 | 321.8244 |
| Tmax (hours) | 4.5 | 6 | 6 | 6 |
| AUC 0-24 hours (ng*h/dL) | 4804.363 | 3586.700664 | 3862.724654 | 4444.852693 |

[a]Actual T3 dose.

Conclusion

The formulations according to the present disclosure IVIVC display delayed release and return to baseline in 24 hours.

Example 4: Dissolution Rate and IVIVC Correlations with T3

Aim

To demonstrate the ability of the formulations according to provide sustained release of triiodothyronine matching the natural variation of hormone levels for T.

Materials and Method

The dissolution rate for formulation D, G, H and I was performed under the same conditions as described in example 2. The amount of T3 was quantified using an ELISA kit according to manufacturer instructions (EliKine™ Triiodothyronine (T3) ELISA Kit, Tebu-bio).

The IVIVC correlations were performed as described in Example 3, updating the mathematical model based on the additional drug release obtained during the dissolution rate test.

Conclusion

The formulations according to the invention provide delayed release of triiodothyronine with a safe return to baseline accommodating for natural circadian rhythm profiles.

Different dosages according to patients needs can be accommodated with the formulations of the present disclosure.

Example 5: Effect of Size and Amount of Matrix

Aim

To study how the size and amount of matrix affects release of active ingredient.

Materials and Method

Formulations with Proxy Molecule Ibuprofen:

Formulations with 5 mg ibuprofen according to formulation A (only PEO in the matrix) were prepared according to example 1 using the VCM method and the dissolution rate was studied as in example 2. Two formulations were prepared:

Round discs: Total weight 942 mg, 3 mm height×20 mm diameter.

Small cylinders: Total weight 301 mg, size 3 mm height×8 mm diameter

Results

Figure 5:
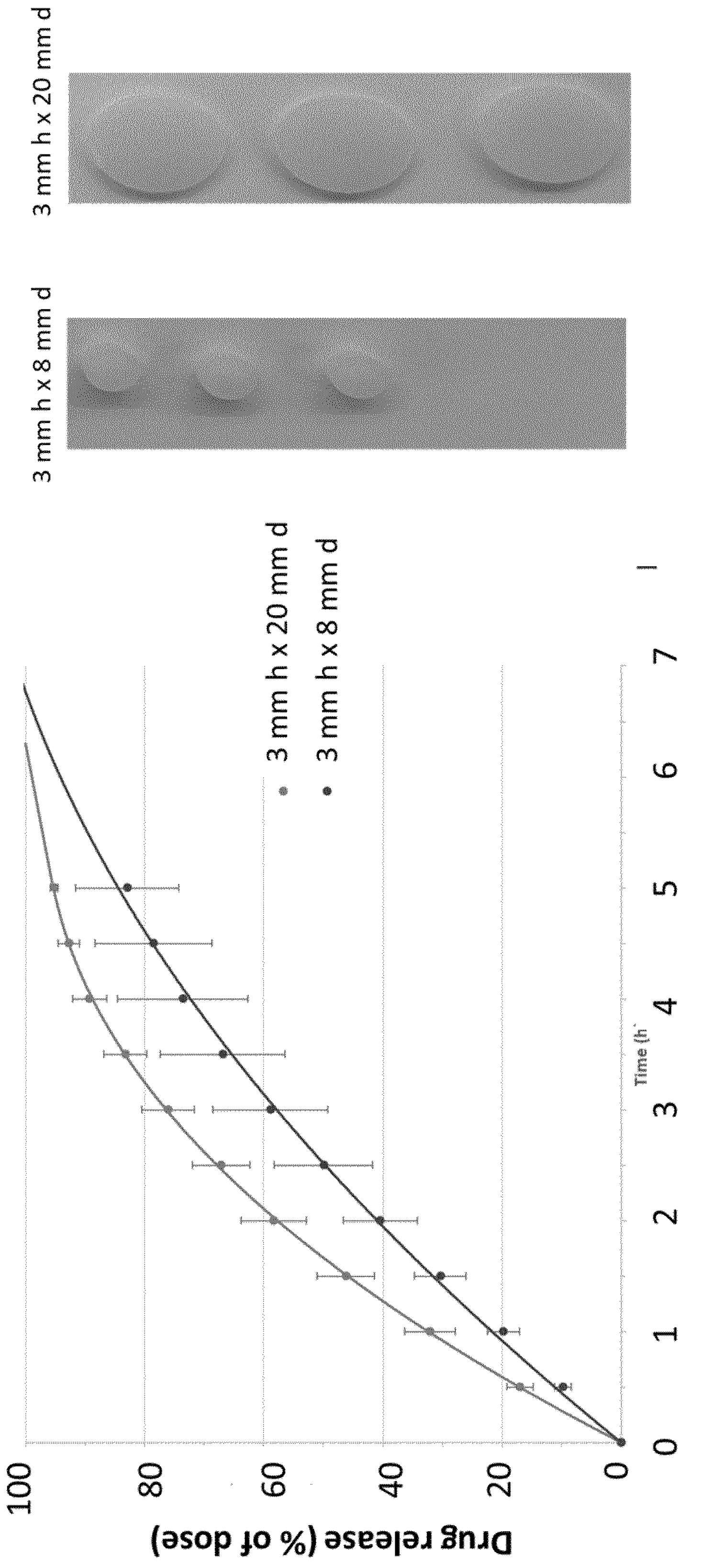
FIG. 5. Dissolution rate of two different ibuprofen tablets with different dimension and amount of matrix, pictures of the tablets included. Dimensions of cylindrical tablets (height mm×diameter mm): round discs 3 mm×20 mm, small cylinders 3 mm×8 mm.

The dissolution profiles (shown in FIG. 5) show that the formulations according to the present disclosure with different geometries and amount of matrix are able to delay drug release within the adequate range.

Conclusion

Different geometries and amounts of matrix provide for adequate sustained release of T3 substitute.

Example 6: Study of Preparation Parameters

Aim

To study the release of ibuprofen (IBU) from different tablets prepared using direct compression at five different compression forces and vacuum compression molding.

Materials and Methods

Six different 8 mm tablet compact formulations were produced and tested in triplicate using a standard dissolution USP2 apparatus. Dissolution of the tablets was done in USP2 vessels with 250 mL 0.1 M phosphate buffer pH 6.8 at 50 rpm. Samples were taken at 30, 60, 90, 120, 150, 180, 210, 240, and 300 min and analysed for ibuprofen content using HPLC. The tablets will be analysed for water penetration and will be imaged through UV imaging.

Results

The compression pressure range tested was—1-7,5 N i.e 20-150 tons/$m^2$. The results show that tablet hardness or deviations in tablet quality at melting temperatures 85-145° C. did I not have an impact on the overall tablet performance, in the stated compression force and temperature limits.

Example 7: Study of Release of Melatonin

Aim

To study the release of melatonin using formulations according to the present disclosure.

Materials and Methods

Two melatonin tablets were prepared using geometric mixing and direct compression according to the following parameters:

Formulation J: 200 mg tablet, 3×8 mm, 5 mg melatonin, 19.5 mg HPMC-AS, 175 mg PEO (n=3)

Formulation K: 500 mg, 3×10 mm, 5 mg melatonin, 49.5 mg HPMC-AS, 445.5 mg PEO

The release was performed in triplicate tablets (n=3) for each formulation intestinal environment as described in Example 2 and melatonin detected using HPLC. The release rate was convoluted to in vivo serum profiles using IVIVC using a method as described in Qureshi et al. 2010[10] with the following assumed parameters: oral bioavailability (BA) is assumed at 15%, Half-life ($T_{1/2}$)=45 min, Volume of distribution (Vd) 1602 L for Body weight (BW) 75 Kg as reported in literature[16].

Results

Figure 7:
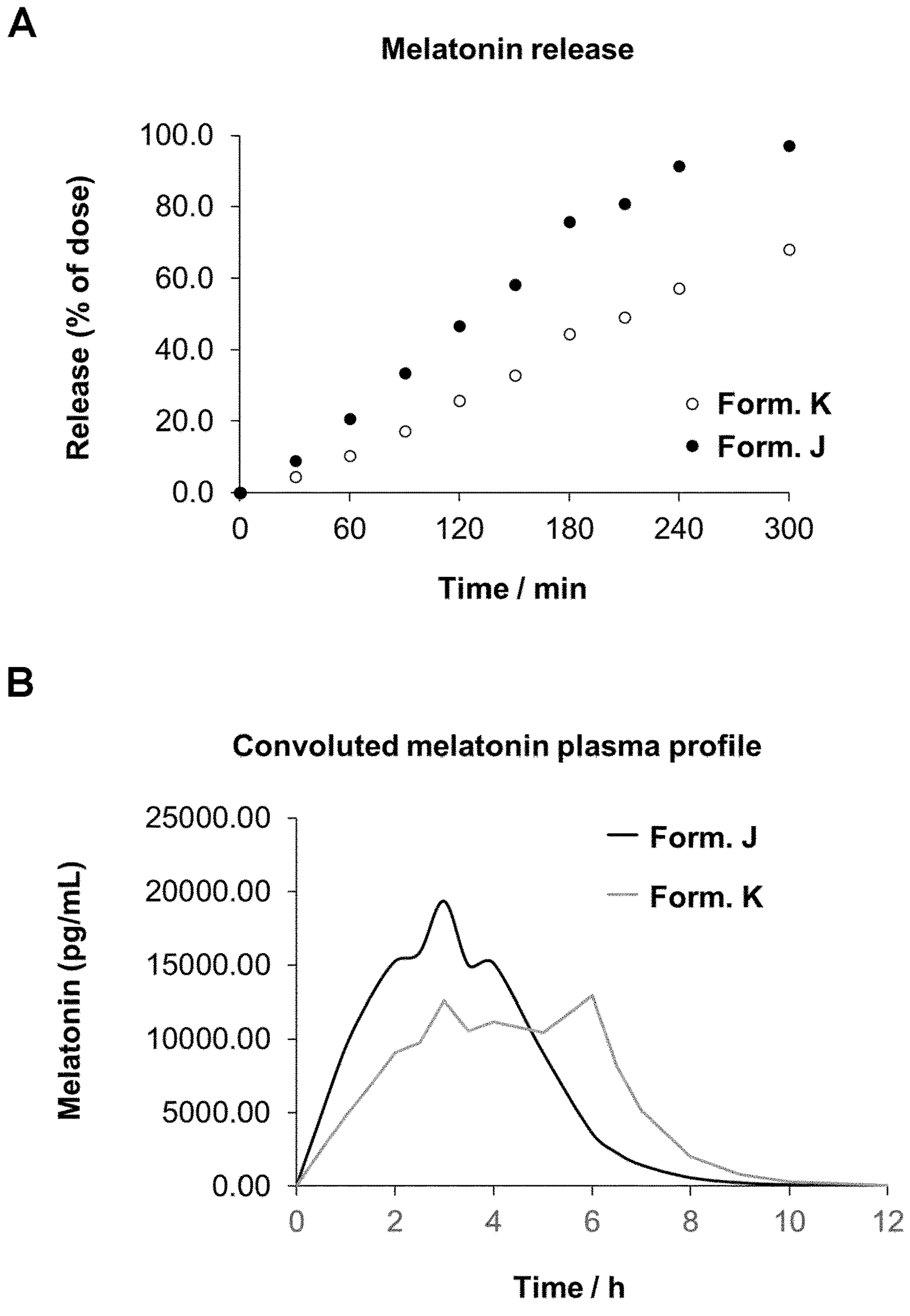
FIG. 7. A Average melatonin release for formulations J and K; B Convoluted IVIVC melatonin plasma profiles for tablets of formulations J and K.

The release rate and convoluted plasma profile are displayed in FIGS. 7A and 7B respectively. The calculated pharmacokinetic parameters are displayed in the following Table:

TABLE 4

Pharmacokinetic (PK) parameters estimated from IVIVC correlations based on dissolution profiles of Formulations J and K with melatonin

| PK parameter | Formulation J | Formulation K |
|---|---|---|
| Tota API (mg) | 5 | 5 |
| Cmax (pg/mL) | 19350 | 12962 |
| Tmax (hours) | 3 | 6 |
| AUC 0-24 hours (pg*h/mL) | 72473 | 68054.9 |

Conclusion

The formulations according to the invention provide delayed release of melatonin with a safe return to baseline accommodating for natural circadian rhythm profiles.

Different formulations according to patients needs can be accommodated with the formulations of the present disclosure.

REFERENCES

1. Muñoz-Ortiz, J., Sierra-Cote, M. C., Zapata-Bravo, E. et al. Prevalence of hyperthyroidism, hypothyroidism, and euthyroidism in thyroid eye disease: a systematic review of the literature. Syst Rev 9, 201 (2020).
2. Hegedüs L, Bianco A C, Jonklaas J, Pearce S H, Weetman A P, Perros P. Primary hypothyroidism and quality of life. Nat Rev Endocrinol. 2022 April; 18(4):230-242.
3. Carlé A, Faber J, Steffensen R, Laurberg P, Nygaard B. Hypothyroid Patients Encoding Combined MCT10 and D102 Gene Polymorphisms May Prefer L-T3+L-T4 Combination Treatment—Data Using a Blind, Randomized, Clinical Study. Eur Thyroid J. 2017 July; 6(3):143-151.
4. W. Russell, R. F. Harrison, N. Smith, K. Darzy, S. Shalet, A. P. Weetman, R. J. Ross, Free Triiodothyronine Has a Distinct Circadian Rhythm That Is Delayed but Parallels Thyrotropin Levels, The Journal of Clinical Endocrinology & Metabolism, Volume 93, Issue 6, 1 Jun. 2008, Pages 2300-2306.
5. Taylor P N, Albrecht D, Scholz A, Gutierrez-Buey G, Lazarus J H, Dayan C M, Okosieme O E. Global epidemiology of hyperthyroidism and hypothyroidism. Nat Rev Endocrinol. 2018 May; 14(5):301-316.
6. Camilla Virili, Alessandro Antonelli, Maria Giulia Santaguida, Salvatore Benvenga, Marco Centanni, Gastrointestinal Malabsorption of Thyroxine, Endocrine Reviews, Volume 40, Issue 1, February 2019, Pages 118-136,
7. Alexandra M. Dumitrescu, Erin C. Hanlon, Marilyn Arosemena, Olga Duchon, Matthew Ettleson, Mihai Giurcanu, and Antonio C. Bianco. Thyroid. February 2022.196-205.
8. Virili C, Brusca N, Capriello S and Centanni M (2021) Levothyroxine Therapy in Gastric Malabsorptive Disorders. Front. Endocrinol. 11:621616.
9. Bowerbank S L, Carlin M G, Dean J R. Dissolution Testing of Single- and Dual-Component Thyroid Hormone Supplements. Separations. 2019; 6(1):18.
10. Qureshi S A. In Vitro-In Vivo Correlation (IVIVC) and Determining Drug Concentrations in Blood from Dissolution Testing—A Simple and Practical Approach. The Open Drug Delivery Journal, 2010, Volume 4

11. Jonklaas J, Burman K D, Wang H, Latham K R. Single-dose T3 administration: kinetics and effects on biochemical and physiological parameters. Ther Drug Monit. 2015; 37(1):110-118.

12. Gamble K L, Berry R, Frank S J, Young M E. Circadian clock control of endocrine factors. Nat Rev Endocrinol. 2014 August; 10(8):466-75.

13. Dumitrescu A M, Hanlon E C, Arosemena M, Duchon O, Ettleson M, Giurcanu M, Bianco A C. Extended Absorption of Liothyronine from Poly-Zinc-Liothyronine: Results from a Phase 1, Double-Blind, Randomized, and Controlled Study in Humans. Thyroid. 2022 February; 32(2):196-205.

14. Handbook of granulation technology, 2nd ed. International Standard Book Number-10: 0-8247-2647-2. Taylor and Francis, 2005.

15. van Tassell et al., "Pharmacokinetics of L-Triiodothyronine in Patients Undergoing Thyroid Hormone Therapy Withdrawal," Thyroid, vol. 29, no. 10, pp. 1371-1379, October 2019, doi: 10.1089/thy.2019.0101.

16. Harpsøe et al. "Clinical pharmacokinetics of melatonin: a systematic review". European Journal of Clinical Pharmacology 71, 901-909 (2015).

The invention claimed is:

1. A composition comprising:

a. triiodothyronine, or a pharmaceutically acceptable salt thereof, b. hydroxypropyl methyl cellulose acetate succinate (HPMC-AS) and/or hydroxypropyl methyl cellulose (HPMC) in a total amount of 0.1% to 20% by weight, and c. polyethylene oxide (PEO) in an amount from 80% to 99.9% by weight.

2. The composition according to claim 1, wherein the triiodothyronine, or a pharmaceutically acceptable salt thereof is present in an amount from 1 μg to 100 μg, or from 5 μg to 50 μg.

3. The composition according to claim 1, wherein the HPMC and/or HPMC-AS is present in an amount from 1% to 20%, or from 5% to 15% by weight.

4. The composition according to claim 1, wherein the HPMC-AS is present in an amount from 1% to 20%, or from 5% to 15% by weight.

5. The composition according to claim 1, wherein the PEO has an average molecular weight from 100 kDa to 500 kDa.

6. The composition according to claim 1, wherein the PEO is present in an amount from 80% to 99%, or from 85% to 95% by weight.

7. The composition according to claim 1, wherein the weight ratio between PEO and the total amount of HPMC and/or HPMC-AS is between 8:2 and 9:0.1.

8. The composition according to claim 1, wherein the triiodothyronine; the HPMC and/or HPMC-AS; and the PEO are in a uniform dispersion.

9. The composition according to claim 1, further comprising one or more additional excipients selected from the group consisting of: binders, fillers, lubricants, release-controlling excipients, antioxidants and preservatives.

10. The composition according to claim 1, further comprising one or more polymers each independently selected from the group consisting of polyethylene oxide, glucomannan, galactan, glucan, polygalacturonic acid, polyhydroxyalkanoates, polyxylane, polygalactomannans, rhanogalacturonan, polyxyloglycan, arabinogalactan, starch, alginates, xhanthan gum, carrageenan, agar, dextran, pectins, cellulose, polyvinyl alcohol, polyvinyl butyral, polyvinyl pyrrolidone, methylcellulose, ethylcellulose, hydroxypropyl cellulose, hydroxypropyl methylcellulose stearate, carboxymethyl cellulose, carbomers, polyacrylic acid, poly (methylacrylic) acid, poly(methylmethacrylate), polyhydroxybutyrate, polyhydroxyvalerate, polyhydroxyphenylvalerate, polylactic acid, polyglycolic acid, a polyacrylic amide, and derivatives or copolymers thereof.

11. The composition according to claim 1, wherein the composition is a solid dosage form.

12. The composition according to claim 1, wherein the composition is selected from a tablet, a mini-tablet or a micro-tablet.

13. The composition according to claim 12, wherein the tablet, the mini-tablet or the micro-tablet is a monolithical tablet or a monolithical cylindrical tablet.

14. The composition according to claim 1, further comprising a coating.

15. The composition according to claim 14, wherein the coating comprises one or more selected from the group consisting of: polyacrylates, polyacrylate derivatives and copolymers thereof, cellulose, cellulose derivatives and shellac.

16. The composition according to claim 1, wherein the composition is a single-unit oral dosage form, or a multiple-unit oral dosage form.

17. A method of treatment of hypothyroidism; or of reducing and/or preventing a side effect of hypothyroidism treatment, comprising administration to a subject in need thereof of a therapeutically effective amount of a composition comprising:

a. triiodothyronine, or a pharmaceutically acceptable salt thereof, b. hydroxypropyl methyl cellulose acetate succinate (HPMC-AS) and/or hydroxypropyl methyl cellulose (HPMC) in a total amount of 0.1% to 20% by weight, and c. polyethylene oxide (PEO) in an amount from 80% to 99.9% by weight.

18. The method according to claim 17, wherein the hypothyroidism is drug induced hypothyroidism, or the hypothyroidism is caused by one or more selected from autoimmune disease, radiation treatment, treatment with other medications, surgical removal of part or all of the thyroid gland, congenital disease and pregnancy.

19. The method according to claim 17, wherein the composition:

a) is administered between 18 h and 00 h;

b) is administered on an empty stomach, or is administered during dinner, or after dinner, wherein administration is up to 3 hours after dinner, c) is administered prior to a major sleep episode, wherein administration is up to 3 hours before a major sleep episode, or d) is administered once daily.

20. The method according to claim 17, wherein the composition:

a) provides an increase in $T_{max}$ of triiodothyronine, as compared to an equivalent amount of triiodothyronine administered as an immediate release formulation, wherein the $T_{max}$ of triiodothyronine is increased by at least 1 hour as compared to an equivalent amount of triiodothyronine administered as an immediate release formulation; and/or, b) provides a $C_{max}$ of triiodothyronine between 150 and 400 ng/dL.

21. A tablet comprising a matrix, said matrix comprising:

a. triiodothyronine, or a pharmaceutically acceptable salt thereof, b. hydroxypropyl methyl cellulose acetate succinate (HPMC-AS) and/or hydroxypropyl methyl cellulose (HPMC) in a total amount of 0.1% to 20% by weight, and c. polyethylene oxide (PEO) in an amount from 80% to 99.9% by weight; wherein the components a), b) and c) are in a uniform dispersion.

* * * * *